(12) United States Patent
Murray et al.

(10) Patent No.: US 12,153,052 B2
(45) Date of Patent: Nov. 26, 2024

(54) IDENTIFICATION AND MONITORING OF IMMUNOGLOBULIN J CHAINS

(71) Applicant: Mayo Foundation for Medical Education and Research, Rochester, MN (US)

(72) Inventors: David L. Murray, Rochester, MN (US); David R. Barnidge, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 862 days.

(21) Appl. No.: 16/646,279

(22) PCT Filed: Sep. 13, 2018

(86) PCT No.: PCT/US2018/050847
§ 371 (c)(1),
(2) Date: Mar. 11, 2020

(87) PCT Pub. No.: WO2019/055632
PCT Pub. Date: Mar. 21, 2019

(65) Prior Publication Data
US 2020/0284800 A1    Sep. 10, 2020

Related U.S. Application Data

(60) Provisional application No. 62/558,023, filed on Sep. 13, 2017.

(51) Int. Cl.
*G01N 33/68*     (2006.01)
*C07K 16/06*     (2006.01)

(52) U.S. Cl.
CPC ....... *G01N 33/6848* (2013.01); *C07K 16/065* (2013.01); *G01N 33/6854* (2013.01); *C07K 2317/22* (2013.01); *C07K 2317/569* (2013.01); *G01N 2800/24* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 8,501,907 B2 | 8/2013 | Jordan et al. |
| 8,679,767 B2 | 3/2014 | Kaur et al. |
| 2002/0182649 A1 | 12/2002 | Weinberger et al. |
| 2003/0027216 A1 | 2/2003 | Kiernan et al. |
| 2005/0009009 A1 | 1/2005 | Peiris et al. |
| 2005/0064422 A1 | 3/2005 | Barnidge et al. |
| 2006/0024296 A1 | 2/2006 | Williams |
| 2006/0281122 A1 | 12/2006 | Bryant |
| 2007/0015222 A1 | 1/2007 | Kaneko et al. |
| 2007/0054407 A1 | 3/2007 | Chen et al. |
| 2007/0105181 A1 | 5/2007 | Pope et al. |
| 2007/0184470 A1 | 8/2007 | Arman et al. |
| 2007/0259398 A1 | 11/2007 | Arnott et al. |
| 2007/0292441 A1 | 12/2007 | Glover et al. |
| 2008/0026949 A1 | 1/2008 | Hoidal et al. |
| 2008/0064055 A1 | 3/2008 | Bryant |
| 2008/0142696 A1 | 6/2008 | Geromanos et al. |
| 2008/0166742 A1 | 7/2008 | Bradwell |
| 2008/0171312 A1 | 7/2008 | Ley et al. |
| 2008/0317745 A1 | 12/2008 | Boruchov et al. |
| 2009/0155280 A1 | 6/2009 | Jordan et al. |
| 2009/0186423 A1 | 7/2009 | Frandsen |
| 2009/0203602 A1 | 8/2009 | Gelber et al. |
| 2009/0258828 A1 | 10/2009 | Beuerman et al. |
| 2010/0015652 A1 | 1/2010 | Granda et al. |
| 2010/0086922 A1 | 4/2010 | Bryant |
| 2010/0167267 A1 | 7/2010 | Schulzknappe et al. |
| 2010/0190652 A1 | 7/2010 | Nagalla et al. |
| 2010/0323381 A1 | 12/2010 | Bergen, III et al. |
| 2011/0065199 A1 | 3/2011 | Kuge et al. |
| 2011/0117021 A1 | 5/2011 | Smith et al. |
| 2011/0151494 A1 | 6/2011 | Koomen et al. |
| 2011/0183426 A1 | 6/2011 | Chan et al. |
| 2011/0294150 A1 | 12/2011 | Koll et al. |
| 2012/0014940 A1 | 1/2012 | Preuss et al. |
| 2012/0309040 A1 | 12/2012 | Madian et al. |
| 2012/0315645 A1 | 12/2012 | Kaur et al. |
| 2012/0322073 A1 | 12/2012 | Lopez-Girona |
| 2013/0040851 A1 | 2/2013 | Hanzawa et al. |
| 2013/0149389 A1 | 6/2013 | Flora et al. |
| 2013/0178370 A1 | 7/2013 | Lavnder et al. |
| 2013/0178385 A1 | 7/2013 | Bahn et al. |
| 2013/0185096 A1 | 7/2013 | Giusti |

(Continued)

FOREIGN PATENT DOCUMENTS

| | | |
|---|---|---|
| CA | 2607197 | 11/2006 |
| CN | 103497254 | 1/2014 |

(Continued)

OTHER PUBLICATIONS

Botz et al., "Detecting monoclonal light chains in urine: micro LC-ESI-Q-TOF mass spectrometry compared to immunofixation electrophoresis," British Journal of Haematology, 167(3):437-8, Nov. 2014.

(Continued)

*Primary Examiner* — Nora M Rooney
(74) *Attorney, Agent, or Firm* — Fish & Richardson P.C.

(57) ABSTRACT

This document relates to materials and methods for identifying and monitoring immunoglobulin J chains in a sample, such as a biological sample, using mass spectrometry techniques.

29 Claims, 11 Drawing Sheets
Specification includes a Sequence Listing.

(56) References Cited

U.S. PATENT DOCUMENTS

| | | |
|---|---|---|
| 2013/0260406 A1 | 10/2013 | Koomen et al. |
| 2013/0302821 A1 | 11/2013 | Sakamoto et al. |
| 2014/0045276 A1 | 2/2014 | Singh et al. |
| 2014/0186332 A1 | 7/2014 | Ezrn et al. |
| 2014/0242072 A1 | 8/2014 | Hansson |
| 2014/0242624 A1 | 8/2014 | Valliere-Douglass |
| 2014/0249049 A1 | 9/2014 | Stoll et al. |
| 2015/0051839 A1 | 2/2015 | Harding et al. |
| 2015/0204884 A1 | 7/2015 | Robblee |
| 2015/0219665 A1 | 8/2015 | Chapple et al. |
| 2015/0276771 A1 | 10/2015 | Madasamy |
| 2015/0340219 A1 | 11/2015 | Mellors |
| 2015/0362506 A1 | 12/2015 | Zhu et al. |
| 2016/0033511 A1 | 2/2016 | Pannell et al. |
| 2016/0041184 A1 | 2/2016 | Barnidge et al. |
| 2016/0047819 A1 | 2/2016 | Viscom et al. |
| 2016/0206660 A1 | 7/2016 | Shi et al. |
| 2016/0231329 A1 | 8/2016 | Olsson et al. |
| 2016/0257763 A1 | 9/2016 | Von Kreudenstein et al. |
| 2016/0349269 A1 | 12/2016 | Hunt et al. |
| 2017/0023584 A1 | 1/2017 | Murray et al. |
| 2017/0044608 A1 | 2/2017 | Wang et al. |
| 2017/0205423 A1 | 7/2017 | Higel et al. |
| 2017/0336419 A1 | 11/2017 | Tran et al. |
| 2018/0106815 A1 | 4/2018 | Barnidge et al. |
| 2018/0267057 A1 | 9/2018 | Barnidge et al. |
| 2019/0195888 A1 | 6/2019 | Barnidge et al. |
| 2020/0003784 A1 | 1/2020 | Murray et al. |
| 2020/0271663 A1 | 8/2020 | Murray et al. |
| 2020/0292556 A1 | 9/2020 | Murray et al. |
| 2020/0341003 A1 | 10/2020 | Murray et al. |

FOREIGN PATENT DOCUMENTS

| | | |
|---|---|---|
| EP | 1329719 | 7/2003 |
| EP | 3270154 | 1/2018 |
| SG | 183701 | 9/2012 |
| WO | WO 2005/101017 | 10/2005 |
| WO | WO 2006/138629 | 12/2006 |
| WO | WO 2008/057083 | 12/2006 |
| WO | WO 2010/119295 | 10/2010 |
| WO | WO 2011/077129 | 6/2011 |
| WO | WO 2012/056232 | 5/2012 |
| WO | WO 2013/049410 | 4/2013 |
| WO | WO 2013/096451 | 6/2013 |
| WO | WO 2013/185180 | 12/2013 |
| WO | WO 2014/078374 | 5/2014 |
| WO | WO 2014/105985 | 7/2014 |
| WO | WO 2014/109927 | 7/2014 |
| WO | WO 2014/121031 | 8/2014 |
| WO | WO 2014/150170 | 9/2014 |
| WO | WO 2015/131169 | 9/2015 |
| WO | WO 2015/154052 | 10/2015 |
| WO | WO 2016/018978 | 2/2016 |
| WO | WO 2016/134365 | 8/2016 |
| WO | WO 2016/172485 | 10/2016 |
| WO | WO 2017/022315 | 2/2017 |
| WO | WO 2017/134274 | 8/2017 |
| WO | WO 2017/144903 | 8/2017 |
| WO | WO 2017/180735 | 10/2017 |
| WO | WO 2017/205694 | 11/2017 |
| WO | WO 2018/049001 | 3/2018 |

OTHER PUBLICATIONS

Dada et al., "High-Resolution Capillary Zone Electrophoresis with Mass Spectrometry Peptide Mapping of Therapeutic Proteins: Peptide Recovery and Post-translational Modification Analysis in Monoclonal Antibodies and Antibody-Drug Conjugates," Anal. Chem. 2017, vol. 89, pp. 11236-11242.

Haeney, M., "Monoclonal Immunoglobulins" in Immunoglobulins in Health and Disease. Immunology and Medicine Series, vol. 1, French M.A.H. (eds). Springer, Dordrecht 1986, 143-172.

Remily-Wood et al. Quantification of Peptides from Immunoglobulin Constant and Variable Regions by Liquid Chromatography-Multiple Reaction Monitoring Mass Spectrometry for Assessment of Multiple Myeloma Patients. Proteonnics Clin Appl. Oct. 2014; 8(0), pp. 783-795. (Year: 2014).

VanDuijn et al., "Quantitative measurement of immunoglobulins and free light chains using mass spectrometry," Analytical chemistry, 87(16):8268-74, Aug. 2015.

Abca3:74m, "Understanding secondary antibodies" 2012, 12 pages, downloaded from http://docs.abcam.com/pdf/general/understanding_secondary_antibodies.pdf.

Abraham et al., "Characterization of free immunoglobulin light chains (LC) by mass spectrometry in light chain-associated (AL) amyloidosis," American Society of Hematology 43rd Annual Meeting, part 2, Orlando, Florida, USA, 98(11 Pt 2), p. 31b, Abstract#3722, Nov. 16, 2001.

Abraham et al., "Correlation of serum immunoglobulin free light chain quantification with urinary Bence Jones protein in light chain myeloma," Clin. Chem., 48(4):655-657, Apr. 2002.

Abraham et al., "Trimolecular complexes of lambda light chain dimers in serum of a patient with multiple myeloma," Clin Chem., 48(10):1805-1811, Oct. 2002.

Acera et al., "Changes in tear protein profile in keratoconus disease," Eye, 25(9):1225-33, Sep. 2011.

Adamczyk et al., "Profiling of polyclonal antibody light chains by liquid chromatography/electrospray ionization mass spectrometry," Rapid Commun Mass Spectrom., 14:49-51, 2000.

Adamczyk et al., "Papain digestion of different mouse IgG subclasses as studied by electrospray mass spectrometry," J Immun Methods., 237:95-104, 2000.

Aisina and Mukhametova, "Structure and Function of Plasminogen/Plasmin System," Russian Journal of Bioorganic Chemistry, 40(6):590-605, Nov. 2014.

Alge et al., "Proteomic Analysis of Plasma Exosome-Associated Proteins Reveals That Differences in Kappa: Lambda Ratios Predict Severe Acute Graft-Versus-Host Disease Early After Allogeneic Hematopoietic Stem Cell Transplantation," Blood., 1278, Nov. 2010.

Alldridge et al., "Proteome profiling of breast tumors by gel electrophoresis and nanoscale electrospray ionization mass spectrometry," J. Proteome. Res., 7(4):1458-1469, Apr. 2008.

Anonymous: "KappaSelect LambdaFabSelect," Data File 28-9448-22 AB, Mar. 1, 2012, Retrieved from the Internet: URL: https://www.gelifesciences.co.jp/catalog/pdf/Kappaselect_LamdaFabSelect.pdf Retrieved on Sep. 22, 2017, 4 pages.

Arun et al., "Immunohistochemical examination of light-chain expression (lambda/kappa ratio) in canine, feline, equine, bovine and porcine plasma cells," Zentralbl Veterinarmed A., 43(9):573-576, Nov. 1996.

Attealnnannan and Levinson et al., "Understanding and Identifying monoclonal gammopathies," Clinical Chemistry, Aug. 2000, 46(8B):1230-1238.

Aucouturier et al., "Monoclonal Ig L chain and L chain V domain fragment crystallization in myeloma-associated Fanconi's syndrome" J. Immunol., 150(8 Pt 1):3561-3568, Apr. 1993.

Aucouturier et al., "Monoclonal immunoglobulin light chains associated to Fanconi's syndrome," Monoclonal Gammopathies and the Kidney, 2003, 87-92.

Awad et al., "Analyses of cerebrospinal fluid in the diagnosis and monitoring of multiple sclerosis," J Neuroimmunol., 219(1-2):1-7, Epub Sep. 25, 2009.

Balakrishnan et al., "Differential proteomic analysis of synovial fluid from rheumatoid arthritis and osteoarthritis patients," Clin. Proteomics., 11(1):1, 2014.

Baldini et al., "Correspondence between salivary proteomic pattern and clinical course in primary Sjögren syndrome and non-Hodgkin's lymphoma: a case report," Journal of translational medicine, 9(1):188, Dec. 2011.

Barnidge and Murray, "Using Mass Spectrometry to Identify IgG Fc and Fab Fragments Produced by Plasmin in Patient Serum," Poster, Presented at American Society for Mass Spectrometry meeting on Jun. 7, 2016.

(56) References Cited

OTHER PUBLICATIONS

Barnidge et al., "Monitoring free light chains in serum using mass spectrometry," Clinical Chemistry and Laboratory Medicine (CCLM). ISSN (Online) 1437-4331, ISSN (Print) 1434-6621, DOI: 10.1515/cclm-2015-0917, Feb. 2016.

Barnidge et al., "Monitoring M-proteins in patients with multiple myeloma using heavy-chain variable region clonotypic peptides and LC-MS/MS," J Proteome Res., 13(4):1905-1910, Epub Mar. 5, 2014.

Barnidge et al., "Phenotyping polyclonal kappa and lambda light chain molecular mass distributions in patient serum using mass spectrometry," J Proteome Res., 13(11):5198-5205, Epub Aug. 26, 2014.

Barnidge et al., "Using MALDI-TOF MS to Screen for Monoclonal Gammopathies in Serum and Urine," 61st Annual ASMS Conference on Mass Spectrometry and Allied Topics, Minneapolis, MN, Jun. 9-13, 2013, 1 page poster.

Barnidge et al., "Using mass spectrometry to monitor monoclonal immunoglobulins in patients with a monoclonal gammopathy," J Proteome Res., 13(3):1419-1427, Epub Feb. 11, 2014.

Barnidge "Monitoring specific IgG tryptic peptides in multiple myeloma using the TripleTOFtm 5600 System," AB SCIEX Annual Users Meeting at ASMS, May 20, 2012, 28 slides.

Barratt et al., "Urine proteomics: the present and future of measuring urinary protein components in disease," CMAJ, 177(4):361-368, Aug. 2007.

Bastian et al., "Intra- and interchain disulfide bridges of the human J chain in secretory immunoglobulin A," Biol. Chem. Hoppe Seyler., 373(12):1255-63, Dec. 1992.

Beck et al., "Characterization of therapeutic antibodies and related products," Anal. Chem., 85(2):715-736, Jan. 2013.

Bennett et al., "Monitoring papain digestion of a monoclonal antibody by electrospray ionization mass spectrometry," Analytical Biochemistry., 245:17-27,1997.

Berg et al., "Mass spectrometry based proteomic analysis identifies two distinct types of cutaneous amyloidosis," Mod Pathol., vol. 22; p. 100A, 2009.

Bergen et al., "Characterization of amyloidogenic immunoglobulin light chains directly from serum by on-line immunoaffinity isolation," Biomedical Chromatography, 18(3):191-201, Apr. 1, 2004.

Bergon et al., "Linearity and detection limit in the measurement of serum M-protein with the capillary zone electrophoresis system Capillarys," Clinical Chemistry and Laboratory Medicine, 43:721-723, 2005.

Bermudez-Crespo et al., "A better understanding of molecular mechanisms underlying human disease," Proteomics Clinical Applications, 1:983-1003, 2007.

Biosis accession No. PREV200200151435, 2 pages, Nov. 2001 Abstract only.

Biosis accession No. PREV201100424453, 2 pages, Nov. 2010 Abstract only.

Bois et al., "Cutaneous amyloidosis: mass spectrometry based proteomic analysis reveals diverse etiology associated with unique histopathological features," Mod Pathol., 26:320A-321A, Feb. 2013.

Boissinot et al., "Up-Regulation of Anti-Inflammatory, STAT3-Activating Hepatocyte Growth Factor and Interleukin-11 in Polycythemia Vera Is Independent of JAK2V617F and Contributes to the Growth of Clonal Erythroblasts," Blood, 116(21):796, Nov. 2010, 52nd Annual Meeting of the American Society of Hematology, Orlando, FL, USA Dec. 4-7, 2010.

Bondarenko et al., "Mass measurement and top-down HPLC/MS analysis of intact monoclonal antibodies on a hybrid linear quadrupole ion trap-orbitrap mass spectrometer," J Am Soc Mass Spectrometry., 20:1415-1424, 2009.

Bourell et al., "Electrospray ionization mass spectrometry of recombinantly engineered antibody fragments," Anal Chem., 66:2088-2095, 1994.

Bradwell et al., "Highly sensitive, automated immunoassay for immunoglobulin free light chains in serum and urine," Clin Chem., 47(4):673-680, Apr. 2001.

Breitkopf et al., "Detection of a rare BCR-ABL tyrosine kinase fusion protein in H929 multiple myeloma cells using immunoprecipitation (IP)-tandem mass spectrometry (MS/MS)," Proc. Natl. Acad. Sci. USA., 109(40):16190-16195, Oct. 2012.

Brochet et al., "IMGT/V-QUEST: the highly customized and integrated system for IG and TR standardized V-J and V-D-J sequence analysis," Nucleic Acids Res., 36(Web Server issue):W503-W508, Epub May 24, 2008.

Butler et al., "Immunoglobulins, antibody repertoire and B cell development," Dev Comp Immunol., 33(3):321-333, Epub Sep. 18, 2008.

Chen et al., "Characterization of protein therapeutics by mass spectrometry: recent developments and future directions," Drug Discovery Today., 16:58-64, 2011.

Cheung et al., "A proteomics approach for the identification and cloning of monoclonal antibodies from serum," Nature Biotechnology., 30:447-452, 2012.

Chevreux et al., "Fast analysis of recombinant monoclonal antibodies using IdeS proteolytic digestion and electrospray mass spectrometry,"Analytical Biochemistry, 415(2):212-214, Aug. 2011.

Chiasserini et al., "CSF proteome analysis in multiple sclerosis patients by two-dimensional electrophoresis," Eur. J. Neurol., 15(9):998-1001, Sep. 2008.

Chow et al., "Serum immune-related proteins are differentially expressed during hibernation in the American black bear," PLoS One, 8(6), 2013.

Chung et al., "Thermodynamic stability of a kappaI immunoglobulin light chain: relevance to multiple myeloma," Biophys. J., 88(6):4232-4242, Jun. 2005.

Cohen et al., "β-Elimination and peptide bond hydrolysis: two distinct mechanisms of human IgG1 hinge fragmentation upon storage," Journal of the American Chemical Society, 129(22):6976-7, Jun. 2007.

Cohen., "Antibody structure," J Clin Path., 28 Suppl, 6:1-7, 1975.

Cordoba et al., "Non-enzymatic hinge region fragmentation of antibodies in solution," J Chromatography B., 818:115-121, 2005.

Coriu et al., "A molecular basis for nonsecretory myeloma," Blood, 104(3):829-831, Aug. 2004.

Cretu, "Identification and Validation of Candidate Soluble Biomarkers for Psoriatic Arthritis Using Quantitative Proteomics (Doctoral dissertation)", 2015.

D'Aguanno et al., "Differential cerebro spinal fluid proteome investigation of Leber hereditary optic neuropathy (LHON) and multiple sclerosis," 193(1-2):156-160, Dec. 2007.

Dai Y, Hu C, Huang Y, Huang Hy, Liu J, Lv T. A proteomic study of peripheral blood mononuclear cells in systemic lupus erythematosus. Lupus. Sep. 2008;17(9):799-804.

Damoc et al., "High resolution proteome analysis of cryoglobulins using Fourier transform-ion cyclotron resonance mass spectrometry," Proteomics, 3(8):1425-1433, Aug. 2003.

De Costa et al., "Sequencing and Quantifying IgG Fragments and Antigen-Binding Regions by Mass Spectrometry" Journal of Proteome Research, 9:2937-2945, Epub Apr. 14, 2010.

De Lorenzi et al., "Urokinase links plasminogen activation and cell adhesion by cleavage of the RGD motif in vitronectin," EMBO reports, 17(7):982-98, Jul. 2016.

Dear et al., "Acquired dysfibrinogenemia caused by monoclonal production of immunoglobulin lambda light chain," Haematologica., 92(11):e111-7, Nov. 2007.

Dekker et al., "An Antibody-Based Biomamarker Discovery Method by Mass Spectrometry Sequencing of Complementarity Determining Regions," Analytical and Bioanalytical Chemistry, 399:1081-1091, 2011.

Deng et al., "Plasma proteomic analysis of pancreatic cancer by 2-dimensional gel electrophoresis," Pancreas, 34(3):310-7, Apr. 2007.

Deshpande et al., "GlycoSpectrumScan: fishing glycopeptides from MS spectra of protease digests of human colostrum sIgA," Journal of proteome research, 9(2):1063-75, Feb. 2010.

Dillon et al., "Optimization of a reversed-phase high-performance liquid chromatography/mass spectrometry method for characterizing recombinant antibody heterogeneity and stability," J. Chromatogr. A., 1120(1-2):112-20, Jul. 2006.

(56) References Cited

OTHER PUBLICATIONS

Dogan et al., "Leukocyte Chemotactic Factor 2 Amyloidosis: A Novel Type of Amyloidosis That Mimics AL Amyloidosis," presented at The United States and Canadian Academy of Pathology Annual Meeting, Mar. 2009, 1 page.
Drożdż et al., "Immunoglobulin cleavage by hypochlorous acid treatment," Clinica. Chimica, acta., 236(2):155-60, May 1995.
Ellias et al., "Proteomic analysis of saliva identifies potential biomarkers for orthodontic tooth movement," The Scientific World Journal, 2012.
Faca et al., "Innovative proteomic approaches for cancer biomarker discovery," Biotechniques, 43(3):279-283, Sep. 2007.
Fan et al., "A single proteolytic cleavage within the lower hinge of trastuzumab reduces immune effector function and in vivo efficacy," Breast Cancer Research, Aug. 2012, 14(4):R116.
Fan et al., "Identification of Niemann-Pick C1 disease biomarkers through sphingolipid profiling," J. Lipid. Res., 54(10):2800-2814, Oct. 2013.
Favereaux et al., "Serum IgG antibodies to P0 dimer and 35 kDa P0 related protein in neuropathy associated with monoclonal gammopathy," J Neurol Neurosurg Psychiatry., 74:1262-1266, 2003.
Fortini et al., "Cerebrospinal fluid oligoclonal bands in the diagnosis of multiple sclerosis. Isoelectric focusing with IgG immunoblotting compared with high-resolution agarose gel electrophoresis and cerebrospinal fluid IgG index," Am J Clin Pathol., 120(5):672-675, Nov. 2003.
Frangione, B., "Structure of Human Immuniglobulins and their Variants" B. Benacerraf (ed) Immunogenetics and Immunodeficiency, 1-53, 1975.
Gadgil et al., "The LC/MS analysis of glycation of IgG molecules in sucrose containing formulations," Jornal of Pharmaceutical Sciences, 96(10):2607-2621, Oct. 2007.
Gebski et al., "Affinity chromatography applications with single-domain antibodies," Bioprocess International., Aug. 1, 2013, Retrieved from the Internet: URL: http://www.bioprocessintl.com/2013/affinity-chromatography-applications-with-single-domain-antibodies-345480/ Retrieved on Sep. 22, 2017.
GenBank Accession AAA59107, "Immunoglobulin lambda light chain C2 region, partial [*Homo sapiens*]," May 4, 2000, 2 pages.
Ghafouri et al., "Newly identified proteins in human nasal lavage fluid from non-smokers and smokers using two-dimensional gel electrophoresis and peptide mass fingerprinting," Proteomics: International Edition, 2(1):112-20, Jan. 2002.
Goetze et al., "High-mannose glycans on the Fc region of therapeutic IgG antibodies increase serum clearance in humans," Glycobiology, 21(7):949-59, Jul. 2011.
Grazio et al., "Differential expression of proteins with heparin affinity in patients with rheumatoid and psoriatic arthritis: a preliminary study," Clin. Exp. Rheumatol., 31(5):665-671, 2013.
Gucinski et al., "Evaluation of intact mass spectrometry for the quantitative analysis of protein therapeutics," Anal. Chem., 84(18):8045-8051, Sep. 2012.
Hagman et al., "Absolute quantification of monoclonal antibodies in biofluids by liquid chromatography-tandem mass spectrometry," Analytical Chemistry, 80(4):1290-1296, Feb. 15, 2008.
Hagmann et al., "Characterization of the F(ab')2 fragment of a murine monoclonal antibody using capillary isoelectric focusing and electrospray ionization mass spectrometry," J Chromatography A., 816:49-58, 1998.
Hanash et al., "Mining the plasma proteome for cancer biomarkers," Nature, 452(7187)571-579, Apr. 2008.
Haraldsson et al., "Determination of kappa and lambda light chains in serum immunoglobulins G, A and M," Ann Clin Biochem., 28 (Pt 5):461-466, Sep. 1991.
Hess et al., "Immunoglobulin cleavage by the streptococcal cysteine protease IdeS can be detected using protein G capture and mass spectrometry," Journal of microbiological methods, Aug. 2007, 70(2):284-91.
Heudi et al., "Towards absolute quantification of therapeutic monoclonal antibody in serum by LC-MS/MS using isotope-labeled antibody standard and protein cleavage isotope dilution mass spectrometry," Anal Chem., 80(11):4200-4207, Epub May 9, 2008.
Hieter et al., "Clustered arrangement of immunoglobuling constant region genes in man," Nature, 294:536-540, 1981.
Hill et al., "Serum free light chains: an alternative to the urine Bence Jones proteins screening test for monoclonal gammopathies," Clin. Chem., 52(9):1743-1748, Sep. 2006.
Holding et al., "Use of serum free light chain analysis and urine protein electrophoresis for detection of monoclonal gammopathies," Clin. Chem. Lab. Med., 49(1):83-88, Jan. 2011.
Hsieh et al., "Elucidation of potential bortezomib response markers in multiple myeloma patients," Journal of Pharmaceutical and Biomedical Analysis, 49:115-122, 2009.
Huang et al., "Site-specific glycosylation of secretory immunoglobulin A from human colostrum. Journal of proteome research," 14(3):1335-49, Mar. 2015.
Huse et al., "Purification of antibodies by affinity chromatography," Journal of biochemical and biophysical methods, 51(3):217-31, May 2002.
Hutchison et al., "The pathogenesis and diagnosis of acute kidney injury in multiple myeloma," Nature Reviews Nephrology, Jan. 2012, 8:43-51.
Iannaccone et al., "Retinal pigment epithelium and microglia express the CD5 antigen-like protein, a novel autoantigen in age-related macular degeneration," Exp Eye Res., 155:64-74, 2017.
International Preliminary Report on Patentability in Application No. PCT/US2018/050847 dated Mar. 17, 2020, 12 pages.
International Search Report & Written Opinion Application No. PCT/US2018/050847 dated Nov. 30, 2018, 20 pages.
Ito and Arata, "Proton nuclear magnetic resonance study on the dynamics of the conformation of the hinge segment of human G1 immunoglobulin," Biochemistry, Nov. 1985, 24(23):6467-74.
Jagannath et al., "Value of serum free light chain testing for the diagnosis and monitoring of monoclonal gammopathies in hematology," Clin Lymphoma Myeloma, 7(8):518-523, Sep. 2007.
Jemal et al., "Cancer statistics, 2003," CA Cancer J Clin., 53(1):5-26, Jan.-Feb. 2003.
Johnson et al., "Cation exchange-HPLC and mass spectrometry reveal C-terminal amidation of an IgG1 heavy chain," Anal. Biochem., 360(1):75-83, Jan. 2007.
Jones et al., "A protocol for 'enhanced pepsin digestion': a step by step method for obtaining pure antibody fragments in high yield from serum," J of Immunol Methods., 275:239-250, 2003.
Joosten et al., "The production of antibody fragments and antibody fusion proteins by yeasts and filamentous fungi," Microbial Cell Factories., 2:1, 15 pages, 2003.
Kabat et al., "An electrophoretic study of the protein components in cerebrospinal fluid and their relationship to the serum proteins," J Clin Invest., 21(5):571-577, Sep. 1942.
Kalaga et al., "Unexpected presence of polyreactive catalytic antibodies in IgG from unimmunized donors and decreased levels in rheumatoid arthritis," J. Immunol., 155(5):2695-2702, Sep. 1995.
Kaltashov et al., "Advances and challenges in analytical characterization of biotechnology products: Mass spectrometry-based approaches to study properties and behavior of protein therapeutics," Biotechnology Advances., 30:210-222, 2012.
Kaplan et al., "Free light chains in plasma of patients with light chain amyloidosis and non-amyloid light chain deposition disease. High proportion and heterogeneity of disulfide-linked monoclonal free light chains as pathogenic features of amyloid disease," British Journal of Haematology., 144(5):705-715, 2008.
Kaplan et al., "Immunoglobulin free light chain dimers in human diseases," The Scientific World Journal, 11:726-735, Mar. 2011.
Kaplan et al., "Isolation and biochemical characterization of plasma monoclonal free light chains in amyloidosis and multiple myeloma: a pilot study of intact and truncated forms of light chains and their charge properties," Clin. Chem. Lab. Med., 46(3)335-341, Mar. 2008.
Katzmann et al., "Serum reference intervals and diagnostic ranges for free kappa and free lambda immunoglobulin light chains: relative sensitivity for detection of monoclonal light chains," Clin. Chem., 48(9):1437-44, Sep. 2002.

(56) References Cited

OTHER PUBLICATIONS

Kim et al., "Prediction of Response to Sorafenib in Hepatocellular Carcinoma: A Putative Marker Panel by Multiple Reaction Monitoring-Mass Spectrometry (MRM-MS)," Mol. Cell Proteomics., 16(7):1312-132, 2017.
Kiselar et al., "Direct Identification of Protein Epitopes by Mass Spectrometry Without Immobilization of Antibody and Isolation of Antibody-Peptide Complexes," Analytical Chemistry, May 1999, 71(9):1792-1801.
Kissel and Mendell, "Neuropathies associated with monoclonal gammopathies," Neuromuscular disorders, Jan. 1996, 6(1):3-18.
Kleennann et al., "Characterization of IgG1 immunoglobulins and peptide-Fc fusion proteins by limited proteolysis in conjunction with LC-MS," Analytical Chemistry, 80(6):2001-2009, Mar. 2008.
Koh et al., "Characterization of exosomes from body fluids of dairy cows," J. Anim. Sci., 95(9):3893-3904, 2017.
Kohlhagen, "Using MALDI-TOF MS to Screen for Monoclonal Proteins in Serum," The Association for Mass Spectrometry Applications to the Clinical Lab [online] 2015. Retrieved from the Internet: <URL: https://www.msacl.org/2015_US_Long_Abstracts/201412041312_53747.pdf>, MSACL 2015 US: Preliminary Conference Program, San Diego, CA, Mar. 28-Apr. 1, 2015, 2 pages.
Kolialexi et al., "Plasma biomarkers for the identification of women at risk for early-onset preeclampsia," Expert Rev. Proteomics., 14(3):269-276, 2017.
Koomen et al., "Proteomic contributions to personalized cancer care," Molecular & Cellular Proteomics, 7.10:1780-1794, 2008.
Kowarik et al., "The cerebrospinal fluid immunoglobulin transcriptome and proteome in neuromyelitis optica reveals central nervous system-specific B cell populations," J Neuroinflammation., 12:19, Jan. 28, 2015.
Kragten et al., "Site-specific analysis of the N-glycans on murine polymeric immunoglobulin A using liquid chromatography/electrospray mass spectrometry," Journal of Mass Spectrometry, 30(12):1679-86, Dec. 1995.
Kroon et al., "Identification of sites of degradation in a therapeutic monoclonal antibody by peptide mapping," Pharmaceutical Research., 9:1386-1393, 1992.
Kurokawa et al., "Macrophage-derived AIM is endocytosed into adipocytes and decreases lipid droplets via inhibition of fatty acid synthase activity," Cell metabolism, 11(6):479-92, Jun. 2010.
Kyle et al., "Criteria for the classification of monoclonal gammopathies, multiple myeloma and related disorders: a report of the International Myeloma Working Group," Br. J. Haematol., 121(5):749-757, Jun. 2003.
Ladwig et al., "Quantification of serum IgG subclasses by use of subclass-specific tryptic peptides and liquid chromatography-tandem mass spectrometry," Clin Chem., 60(8):1080-1088, May 5, 2014.
Landgren et al., "Monoclonal gammopathy of undetermined significance (MGUS) consistently precedes multiple myeloma: a prospective study" Blood, 113(22):5412-5417, May 28, 2009.
Lavatelli et al., "A novel approach for the purification and proteomic analysis of pathogenic immunoglobulin free light chains from serum," Biochimica rt Biophysica Acta., 1814(3):409-419, Mar. 2011.
Lebeau et al., "Generalized crystal-storing histiocytosis associated with monoclonal gammopathy: molecular analysis of a disorder with rapid clinical course and review of the literature," Blood., 100:1817-1827, 2002.
Lee et al., "Relationship between Group-Specific Component Protein and the Development of Asthma," American journal of respiratory and critical care medicine 184(5):528-536, 2011.
Lefranc, "IMGT, the International ImMunoGeneTics Information System," Cold Spring Harb Protoc., 2011(6):595-603, Jun. 1, 2011.
Legros et al., "Characterization of an anti-Borrelia burgdorferi OspA conformational epitope by limited proteolysis of monoclonal antibody-bound antigen and mass spectrometric peptide mapping," Protein Science, 9(5):1002-10, May 2000.
Leung et al., "A novel and rapid approach to protein expression profiling of cerebrospinal fluid (CSF) from medulloblastoma patients using functionalized magnetic beads, AnchorChipTM technology, MALDI-TOf and MALDI-TOF/TOF mass spectrometry," 33rd Meeting of the Society of Neuroscience, 751.3, Nov. 2003.
Leung et al., "Monoclonal gammopathy of renal significance: when MGUS is no longer undetermined or insignificant," Blood, 120:4292-4295, 2012.
Li et al., "General LC-MS/MS method approach to quantify therapeutic monoclonal antibodies using a common whole antibody internal standard with application to preclinical studies," Analytical Chemistry, 84:1267-1273, 2012.
Li et al., "Simultaneous analysis of multiple monoclonal antibody biotherapeutics by LC-MS/MS method in rat plasma following cassette-dosing," AAPS J., 15(2):337-346, Epub Dec. 12, 2012.
Lill et al., "Microwave-assisted proteomics," Mass spectrometry reviews, 26(5):657-71, Sep. 2007.
Lim et al., "Identification and Location of a Cysteinyl Post-translational Modification in an Amyloidogenic kappa1 Light Chain Protein by Electrospray Ionization and Matrix-Assisted Laser Desorption/Ionization Mass Spectrometry," Analytical Biochemistry, Aug. 2001, 295:45-56.
Lindop et al., "Molecular signature of a public clonotypic autoantibody in primary Sjogren's syndrome: A "forbidden" clone in systemic autoimmunity," Arthritis & Rheumatism., 63(11):3477-3486, Oct. 28, 2011.
Liu et al., "Analysis of plasma proteome from cases of the different traditional Chinese medicine syndromes in patients with chronic hepatitis B," Journal of Pharmaceutical and Biomedical Analysis, 59:173-178, 2012.
Liu et al., "Quantitation of a recombinant monoclonal antibody in monkey serum by liquid chromatography-mass spectrometry," Anal Biochem., 414(1):147-153, Epub Mar. 8, 2011.
Lokamani et al., "Gelsolin and ceruloplasmin as potential predictive biomarkers for cervical cancer by 2D-DIGE proteomics analysis," Pathology & Oncology Research, 20(1):119-29, Jan. 2014.
Lu et al., "Detection of abundant proteins in multiple myeloma cells by proteomics," J Proteomics Bioinform., 3(1):005-009, 2010.
Lu et al., "LC-MS Analysis of Polyclonal Human Anti-Neu5Gc Xeno-Autoantibodies Inmunoglobulin G Subclass and Partial Sequence Using Multistep Intravenous Immunoglobulin Affinity Purification and Multienzymatic Digestion," Analytical Chemistry., 84(6):2761-2768, Mar. 20, 2012.
Marien et al., "Detection of monoclonal proteins in sera by capillary zone electrophoresis and free light chain measurements," Clin. Chem., 48(9):1600-1601, Sep. 2002.
Markowitz, "Dysproteinemia and the Kidney," Advances in Anatomic Pathology, Jan. 2004, 11:49-63.
Mazur et al., "A platform for characterizing therapeutic monoclonal antibody breakdown products by 2D chromatography and top-down mass spectrometry," The AAPS journal, 14(3):530-41, Sep. 2012.
McBride et al., "Chromosomal location of human kappa and lambda immunoglobulin light chain constant region genes," J Exp Med., 155(5):1480-1490, May 1, 1982.
Merlini and Palladini, "Differential diagnosis of monoclonal gammopathy of undetermined significance" Hematology, 595-603, 2012.
Micallef, J. et al., Journal of Hennatology & Oncology 2010, 3, 11 pages.
Mills et al., "Using mass spectrometry to quantify rituximab and perform individualized immunoglobulin phenotyping in ANCA-associated vasculitis," Analytical chemistry, 88(12):6317-25, Jun. 2016.
Minnura et al., "Contrasting glycosylation profiles between Fab and Fc of a human IgG protein studied by electrospray ionization mass spectrometry," J. Immunol. Methods., 326(1-2):116-26, Sep. 2007.
Mischak et al., "Urinary proteome analysis using capillary electrophoresis coupled to mass spectrometry: a powerful tool in clinical diagnosis, prognosis and therapy evaluation," Journal of Medical Biochemistry, Oct. 2009, 28(4):223-234.
Mitchell et al., "Alterations in the bovine bronchoalveolar lavage proteome induced by dexamethasone," Veterinary immunology and immunopathology, 118(3-4):283-93, Aug. 2007.

(56) References Cited

OTHER PUBLICATIONS

Moh et al., "Site-specific N-glycosylation of recombinant pentameric and hexameric human IgM," Journal of The American Society for Mass Spectrometry, 27(7):1143-55, Apr. 2016.
Mohr et al., "High-efficiency nano- and micro-HPLC—high-resolution Orbitrap-MS platform for top-down proteomics," Proteomics., 10(20):3598-3609, Oct. 2010.
Mukhopadhyay et al., "A tribute to Frank Anscombe and random central limit theorem from 1952," Sequential Analysis, 31(3): 265-277, 2012.
Murphy et al., "Characterization of systemic amyloid deposits by mass spectrometry," Methods Enzymol., 412:48-62, 2006.
Murray et al., "Characterization of immunoglobulin by mass spectrometry with applications for the clinical laboratory," Crit. Rev. Clin Lab. Sci., 50(4-5):91-102, Jul.-Oct. 2013.
Nasr et al., "Immunotactoid glomerulopathy: clinicopathologic and proteomic study," Nephrol Dial Transplant., 27(11):4137-4146, Epub Aug. 7, 2012.
Obermeier et al., "Matching of oligoclonal immunoglobulin transcriptomes and proteomes of cerebrospinal fluid in multiple sclerosis," Nat Med., 14(6):688-693, Epub May 18, 2008.
Oeckl et al., "CSF concentrations of cAMP and cGMP are lower in patients with Creutzfeldt-Jakob disease but not Parkinson's disease and amyotrophic lateral sclerosis," PLoS One, 7(3):e32664, Mar. 2012.
Okamoto et al., "Proteome analysis of bronchoalveolar lavage fluid in chronic hypersensitivity pneumonitis," Allergology International, 61(1):83-92, Jan. 2012.
Oruc et al., "IgA structure variations associate with immune stimulations and IgA mesangial deposition," Journal of the American Society of Nephrology, 27(9):2748-61, Sep. 2016.
Pabst et al., "A microarray-matrix-assisted laser desorption/ionization-mass spectrometry approach for site-specific protein N-glycosylation analysis, as demonstrated for human serum immunoglobulin M (IgM)," Molecular & Cellular Proteomics, 14(6):1645-56, Jun. 2015.
Pang et al., "Biomarker discovery in urine by proteomics," Journal of Proteome Research, 1:161-169, Epub Feb. 16, 2002.
Persson et al., "Development of Mass Spectrometry Based Techniques for the Identification and Determination of Compositional Variability in Recombinant Polyclonal Antibody Products," Analytical Chemistry, Sep. 2010, 82(17):7274-7282.
Piehler et al., "Quantitation of serum free light chains in combination with protein electrophoresis and clinical information for diagnosing multiple myeloma in a general hospital population," Clin. Chem., 54(11):1823-1830, Nov. 2008.
Qin et al., "Development of a "reverse capture" autoantibody microarray for studies of antigen-autoantibody profiling," Proteomics., 6(10):3199-209, May 2006.
Radovic, V. V.,"Recommendations for Use of Free Light Chain Assay in Monoclonal Gammopathies" Journal of Medical Biochemistry, 29:1-8, 2010.
Rajkumar et al., "Advances in the diagnosis, classification, risk stratification, and management of monoclonal gammopathy of undetermined significance: implications for recategorizing disease entities in the presence of evolving scientific evidence," Mayo Clinic Proceedings., 85:945-948, 2010.
Reid et al., "Rapid whole monoclonal antibody analysis by mass spectrometry: An ultra scale-down study of the effect of harvesting by centrifugation on the post-translational modification profile," Biotechnology and Bioengineering, 107(1):85-95, Sep. 2010.
Remily-Wood et al., "A database of reaction monitoring mass spectrometry assays for elucidating therapeutic response in cancer," Proteomics Clinical Applications, 5:383-396, 2011.
Ren et al., "Reversed-phase liquid chromatography-mass spectrometry of site-specific chemical modifications in intact immunoglobulin molecules and their fragments," J Chromatography A., 1179:198-204, 2008.
Roberts et al., "An Integrated Strategy for Structural Characterization of the Protein and Carbohydrate Components of Monoclonal Antibodies: Application to Anti-Respiratory Syncytial Virus Mab," Analytical Chemistry, Oct. 1995, 67(20):3613-3625.
Rodriguez et al., "Immunoglobulin derived depositions in the nervous system: novel mass spectrometry application for protein characterization in formalin-fixed tissues," Lab Invest., 88(10):1024-1037, Epub Aug. 18, 2008.
Rosati et al., "Exploring an orbitrap analyzer for the characterization of intact antibodies by native mass spectrometry," Angew. Chem. Int. Ed. Engl., 51(52):12992-12996, Dec. 2012.
Ruan et al., "Strategy and its implications of protein bioanalysis utilizing high-resolution mass spectrometric detection of intact protein," Anal. Chem., 83(23):8937-8944, Dec. 2011.
Salinas et al., "Buffer-dependent fragmentation of a humanized full-length monoclonal antibody," Journal of pharmaceutical sciences, 99(7):2962-74, Jul. 2010.
Sandoval et al., "Rapid removal of N-linked oligosaccharides using microwave assisted enzyme catalyzed deglycosylation," International Journal of Mass Spectrometry, 259(1-3):117-23, Jan. 2007.
Sanjurjo et al., "ATM/CD5L: a key protein in the control of immune homeostasis and inflammatory disease," J. Leukoc. Biol., 98(2):173-184, Aug. 2015.
Sarrias et al., "Biochemical characterization of recombinant and circulating human Spα," Tissue antigens, Apr. 2004, 63(4):335-44.
Schaefer et al., "Residual serum monoclonal protein predicts progression-free survival in patients with previously untreated multiple myeloma," Cancer., 116:640-646, 2010.
Sethi et al., "Mass spectrometry-based proteomic diagnosis of renal immunoglobulin heavy chain amyloidosis," Clin J Am Soc Nephrol., 5:2180-2187, 2010.
Shaheen et al., "Multiple Myeloma and Immunosecretory Disorders: An Update," Advances in Anatomic Pathology, Jul. 2008, 15(4):196-210.
Sikkink et al., "Biochemical and Aggregation Analysis of Bence Jones Proteins From Different Light Chain Diseases," Amyloid, Mar. 2008, 15:29-39.
Singh et al., "Cerebrospinal-fluid-derived immunoglobulin G of different multiple sclerosis patients shares mutated sequences in complementarity determining regions," Mol Cell Proteomics, 12(12):3924-3934, Epub Aug. 22, 2013.
Skriner et al., "Association of citrullinated proteins with synovial exosomes," Arthritis & Rheumatism: Official Journal of the American College of Rheumatology, Dec. 2006, 54(12):3809-14.
Sloane et al., "Proteomic analysis of sputum from adults and children with cystic fibrosis and from control subjects. American journal of respiratory and critical care medicine," Dec. 2005, 172(11):1416-26.
Song et al., "Characterization of N-terminal processing of group VIA phospholipase A2 and of potential cleavage sites of amyloid precursor protein constructs by automated identification of signature peptides in LC/MS/MS analyses of proteolytic digests," J Am Soc Mass Spectrom., 15(12):1780-1793, Dec. 2004.
Stoop et al., "Quantitative MALDI-FT-ICR analysis of cerebrospinal fluid of relapsing-remitting and primary progressive multiple sclerosis patients," Multiple Sclerosis., 15(9):S83, Sep. 2009.
Stubbs et al., "Anti-neurofilament antibodies in neuropathy with monoclonal gammopathy of undetermined significance produce experimental motor nerve conduction block," Acta Neuropathology., 105:109-116, 2003.
Sun et al., "Immunoglobulin genes and diversity: what we have learned from domestic animals," J Anim Sci Biotechnol., 3(1):18, Jun. 20, 2012.
Sun et al., "Preparation and mass spectrometric study of egg yolk antibody (IgY) against rabies virus," Rapid communications in mass spectrometry, 15(9):708-12, May 2001.
Theis et al., "Immunoglobulin Light Chain Gene Constant Region Is An Invariable Part of Amyloid Deposits in AL Amyloidosis," Blood, 112(11):3128, Nov. 16, 2008.
Theis et al., "Mass spectrometry based proteomic analysis of AL amyloidosis: Immunoglobulin Light Chain Gene Constant Region Is An Invariable Part of Amyloid Deposits and provides valuable diagnostic target," presented at The United States and Canadian Academy of Pathology Annual Meeting, Mar. 2009, 1 page.

(56) References Cited

OTHER PUBLICATIONS

Thermo Scientific, "MelonTM Gel IgG Spin Purification Kit" [online], 2011 [retrieved on Aug. 6, 2015], Retrieved from the Internet: <URL: https://tools.lifetechnologies.com/content/sfs/manuals/MAN0011513_Melon_Gel_IgG_Spin_Purif_UG.pdf>, 4 pages.
Thurgood et al., "An Immunodominant La/SSB autoantibody proteome derives from public clonotypes," Clinical and Experimental Immunology., 174:237-244, Oct. 6, 2013.
Tissot et al., "IgM Are Associated to Sp Alpha (CD5 Antigen-Like)," Electrophoresis, 23(7-8):1203-1206, Apr. 2002.
VanDuijn et al., "Immune responses are characterized by specific shared immunoglobulin peptides that can be detected by proteomic techniques," Journal of Biological Chemistry, 285:29247-29253, Jul. 8, 2010.
Vase et al., "A57 Proteomic profiling of pretreatment serum from HIV-infected patients identifies candidate markers predictive of lymphoma development," AIDS, 2016, 30(12):1889-1898.
Verheesen et al., "Beneficial properties of single-domain antibody fragments for application in immunoaffinity purification and immunoperfusion chromatography," Biochim Biophys Acta., 1624(1-3):21-28, Dec. 5, 2003.
Vlasak and Ionescu, 2011, mAbs 3:253-263.
Vrana et al., "Classification of amyloidosis by laser microdissection and mass spectrometry-based proteomic analysis in clinical biopsy specimens," Blood, 114(24):4957-4960, Dec. 2009.
Vrana et al., "Amyloidosis typing based on Laser Microdissection and Mass Spectrometry of Paraffin-Embedded Tissue Biopsies" Companion to Peripheral Neuropathy, pp. 347-349, 2010.
Vrana et al., "Classification of Amyloidosis in Fat Aspiration Specimens Using Mass Spectrometry Based Proteomics," presented at The United States and Canadian Academy of Pathology Annual Meeting, Mar. 2009, 1 page.
Vrana et al., "Diagnosis and Classification of Amyloidosis in Abdominal Subcutaneous Fat Aspiration Specimens Using Mass Spectrometry Based Proteomics," Blood, 112(11):2710, Nov. 16, 2008.
Vrana et al., "Diagnosis and Typing of Cardiac Amyloidosis in Routine Clinical Specimens by Mass Spectrometry Based Proteomic Analysis," presented at The United States and Canadian Academy of Pathology Annual Meeting, Mar. 2009, 1 page.
Wagner-Rousset et al., "The way forward, enhanced characterization of therapeutic antibody glycosylation: comparison of three level mass spectrometry-based strategies," Journal of Chromatography B, 872(1-2):23-37, Sep. 2008.
Wang et al., "Construction of a Multiple Myeloma Diagnostic Model by Magnetic Bead-Based MALDI-TOF Mass Spectrometry of Serum and Pattern Recognition Software" Anatomical Record, 292:604-610, 2009.
Wang et al., "Differentiation and quantification of endogenous and recombinant-methionyl human leptin in clinical plasma samples by immunocapture/mass spectrometry," J. Pharm. Biomed. Anal., 70:440-446, Nov. 2012.
Wang et al., "Discovery of potential colorectal cancer serum biomarkers through quantitative proteomics on the colonic tissue interstitial fluids from the AOM-DSS mouse model," J. Proteomics, 2016, 132:31-40.
Wang et al., "Molecular basis of assembly and activation of complement component C1 in complex with immunoglobulin G1 and antigen," Molecular cell, 63(1):135-45, Jul. 2016.
Wang et al., "Structural Characterization of a Recombinant Monoclonal Antibody by Electrospray Time-Of-Flight Mass Spectrometry," Pharmaceutical Research, Aug. 2005, 22(8):1338-1349.
Whiteaker et al., "Sequential multiplexed analyte quantification using peptide immunoaffinity enrichment coupled to mass spectrometry," Mol Cell Proteomics., 11(6):10.1074/mcp.M111.015347, 2012, 10 pages.
Willrich et al., "Quantitation of infliximab using clonotypic peptides and selective reaction monitoring by LC-MS/MS," International Immunopharmacology., 28(1):513-520, Sep. 1, 2015.
Willrich et al., "Serum infliximab quantitation by LC-MS/MS in patients treated for inflammatory disorders," Gastroenterology AGA Abstracts., Sa1252, May 1, 2014, Retrieved from the internet: URL:https://ac.els-cdn.com/S0016508514608568/1-S2.0-S0016508514608568-main.pdf?_ti d=e58e3b4c-caOa-11e7-96b2-OOOO0aabOf6b&acdnat-1510753563_74ab7a6bOb5f976b8c948a995d894fce, Retrieved on Nov. 15, 2017, Abstract Only.
Wine, Y. et al. Molecular deconvolution of the monoclonal antibodies that comprise the polyclonal serum response, PNAS vol. 110, No. 8, pp. 2993-2998 (Year: 2013).
Xu et al., "Discovery and identification of serum potential biomarkers for pulmonary tuberculosis using iTRAQ-coupled two-dimensional LC-MS/MS," Proteomics, 2014, 14(2-3):322-331.
Yamazaki et al., "A proteolytic modification of AIM promotes its renal excretion," Scientific Reports, 6:38762, Dec. 2016.
Yin et al., "Protein biomarkers of new-onset cardiovascular disease: prospective study from the systems approach to biomarker research in cardiovascular disease initiative," Arterioscler. Thromb. Vasc. Biol., 2014, 34(4):939-945.
Zhang et al., "Characterization of variable regions of monoclonal antibodies by top-down mass spectrometry," Anal Chem., 79(15):5723-5729, 2007.
Zhang et al., "Proteomic analysis of plasma in adult active pulmonary tuberculosis patients with diabetes mellitus," The FASEB Journal, Apr. 2015, 29(1 supplement):275-7.
Zhaoyu et al., "Alteration of DBP levels in CSF of patients with MS by proteomics analysis," Cell Mol. Neurobiol., 29(2):203-210, Mar. 2009.
Zhong et al., "Microwave-assisted acid hydrolysis of proteins combined with liquid chromatography MALDI MS/MS for protein identification," Journal of the American Society for Mass Spectrometry, Apr. 2005, 16(4):471-81.
Zhong et al., "Protein sequencing by mass analysis of polypeptide ladders after controlled protein hydrolysis," Nature biotechnology, Oct. 2004, 22(10):1291-6.
Zhou et al., "Quantitative analysis of N-linked glycoproteins in tear fluid of climatic droplet keratopathy by glycopeptide capture and iTRAQ," Journal of proteome research, Apr. 2009, 8(4):1992-2003.
U.S. Appl. No. 12/866,709, filed Aug. 17, 2010, Harold R. Bergen, III, Abandoned.
U.S. Appl. No. 14/777,236, filed Sep. 15, 2015, David R. Barnidge, Published.
U.S. Appl. No. 15/301,633, filed Oct. 3, 2016, David L. Murray, Issued.
U.S. Appl. No. 16/297,340, filed Mar. 8, 2019, David L. Murray, Allowed.
U.S. Appl. No. 15/329,512, filed Jan. 26, 2017, David R. Barnidge, Issued.
U.S. Appl. No. 16/646,289, filed Mar. 11, 2020, David L. Murray, Pending.
U.S. Appl. No. 16/646,296, filed Mar. 11, 2020, David L. Murray, Pending.
U.S. Appl. No. 16/331,228, filed Mar. 7, 2019, David R. Barnidge, Published.
U.S. Appl. No. 15/762,900, filed Mar. 23, 2018, David R. Barnidge, Published.
Baenziger, "Structure of the oligosaccharide of human J chain," J. Biol. Chemistry, May 25, 1979, 254(10):4063-4071.
Cutillas, P. R. et al, Clinical Science 2003, 104, 483-490.
Hutchison. C. A. et al, Clinical Journal of the American Society of Nephrology 2008, 3, 1684-1690.
Johansen et al.. "Role of J Chain in Secretory Immunoglobulin Formation," Scand. J. Immunology, Sep. 2000, 52(3):240-248.
Matheson et al., "Light chain-deficient mice produce novel multimeric heavy-chain-only IgA by faulty class switching." Int. Immunology. Aug. 2009. 21(8):957-966.
U.S. Appl. No. 16/930,790, filed Jul. 16, 2020, David L. Murray, Published.
Ankeny et al., "B cells produce pathogenic antibodies and impair recovery after spinal cord injury in mice," Journal of Clinical Investigation, Oct. 2009, 119(10):2990-2999.

(56) References Cited

OTHER PUBLICATIONS

Attaelmannan et al., "Understanding and Identifying Monoclonal Gammopathies," Clinical Chemistry, 2000, 46(8B):1230-1238.
Bhattacharyya et al., "Biomarkers that discriminate multiple myeloma patients with or without skeletal involvement detected using SELDI-TOF mass spectrometry and statistical and machine learning tools," Disease Markers, 2006, 22:245-255.
Cumova et al., "Proteomic Analysis in Multiple Myeloma Research," Molecular Biotechnology, 2011, 47:83-93.
Fang et al., "Affinity separation and enrichment methods in proteomic analysis," Journal of Proteomics, 2008, 71:284-303.
Lu et al., "Development of Different Analysis Platforms with LC-MS for Pharmacokinetic Studies of Protein Drugs," Analytical Chemistry, Nov. 2009, 81(21):8715-8723.
Perdivara, "Structure Determination of Autoimmune Disease—Related Proteins by High Performance Liquid Chromatography—Mass Spectrometry," Dissertation for the degree of Doctor of Natural Sciences, University of Konstanz, 2009, 185 pages.
Siuti et al., "Decoding protein modifications using top-down mass spectrometry," Nature Methods, Oct. 2007, 4(10):817-821.
Tissot et al., "High-resolution two-dimensional protein electrophoresis of pathological plasma/serum," Applied and Theoretical Electrophoresis, 1991, 2:7-12.
Tsai et al., "Origin of the Isoelectric Heterogeneity of Monoclonal Immunoglobulin h1B4," Pharmaceutical Research, 1993, 10(11):1580-1586.
Hong et al., "A Method for Comprehensive Glycosite-Mapping and Direct Quantitation of Serum Glycoproteins," J. Proteome Res., Dec. 2015, 14(12):5179-5192.
Alvarez et al., "On-line characterization of monoclonal antibody variants by liquid chromatography-mass spectrometry operating in a two-dimensional format," Anal. Biochem., Dec. 2011, 419(1):17-25.
Baumann et al., "Standardized approach to proteome profiling of human serum based on magnetic bead separation and matrix-assisted laser desorption/ionization time-of- flight mass spectrometry," Clin. Chem., Jun. 2005, 51(6):973-980.
Brady et al., "Molecular mass analysis of antibodies by on-line Sec-Ms," J. Am. Soc. Mass Spectrom., Apr. 2008, 19(4):502-509.
Breen et al., "High-throughput fractionation of human plasma for fast enrichment of low- and high-abundance proteins," Blood Transfus., May 2012, 10(Suppl. 2):s89- 100.
Dillon et al., "Development of an analytical reversed-phase high-performance liquid chromatography-electrospray ionization mass spectrometry method for characterization of recombinant antibodies," J. Chromatogr., Oct. 2004, 1053(1-2):299-305.
Gadgil et al., "Improving mass accuracy of high performance liquid chromatography/electrospray ionization time-of-flight mass spectrometry of intact antibodies," J. Am. Soc. Mass Spectrom., Jun. 2006, 17(6):867-872.
Hale, "Advantageous Uses of Mass Spectrometry for the Quantification of Proteins," Int. J. Proteomics, Jan. 2013, 2013:219452, 6 pages.
Hao et al., "A Complete Workflow Solution for Intact Monoclonal Antibody Characterization Using a New High-Performance Benchtop Quadrupole-Orbitrap Lc- Ms/Ms," Thermo Scientifc Poster Note, 2012, 9 pages.
Huschka et al., "Rapid separation of immunoglobulin M by immunoaffinity chromatography for detection of specific antibodies to rubella and Treponema pallidum," Eur. J. Clin. Microbiol., Apr. 1982, 1(2): 118-121.
Janin-Bussat et al., "Structural Characterization of Antibodies by Mass Spectrometry," Kontermann and Dubel (eds.), Antibody Engineering, vol. 1, 2010, pp. 613-634.
Le et al., "Trap for MAbs: characterization of intact monoclonal antibodies using reversed-phase HPLC on-line with ion-trap mass spectrometry," J. Am. Soc. Mass Spectrom., Mar. 2005, 16(3):307-311.
Liu et al., "Analysis of reduced monoclonal antibodies using size exclusion chromatography coupled with mass spectrometry," J. Am. Soc. Mass Spectrom., Dec. 2009, 20(12):2258-2264.
Lyubarskaya et al., "Analysis of recombinant monoclonal antibody isoforms by electrospray ionization mass spectrometry as a strategy for streamlining characterization of recombinant monoclonal antibody charge heterogeneity," Anal. Biochem., Jan. 2006, 348(1):24-39.
Nevens et al., "Affinity chromatographic purification of immunoglobulin M antibodies utilizing immobilized mannan binding protein," J. Chromatogr., Apr. 1992, 597(1-2):247-256.
Nikolayenko et al., "Preparation of highly purified human IgG, IgM, and IgA for immunization and immunoanalysis," Ukrainica Bioorganica Acta, 2005, 2:3-11.
Olivova et al., "Determination of N-glycosylation sites and site heterogeneity in a monoclonal antibody by electrospray quadrupole ion-mobility time-of-flight mass spectrometry," Rapid Commun. Mass Spectrom., Jan. 2008, 22(1):29-40.
Rosati et al., "Qualitative and semiquantitative analysis of composite mixtures of antibodies by native mass spectrometry," Anal. Chem., Aug. 2012, 84(16):7227- 7232.
Rose et al., "High-sensitivity Orbitrap mass analysis of intact macromolecular assemblies," Nat. Methods, Nov. 2012, 9(11): 1084-1086, with 2 pages of supplementary material.
Zhang et al., "Structural characterization of intact antibodies by high-resolution LTQ Orbitrap mass spectrometry," J. Mass Spectrom., Jan. 2010, 45(1):112-120.

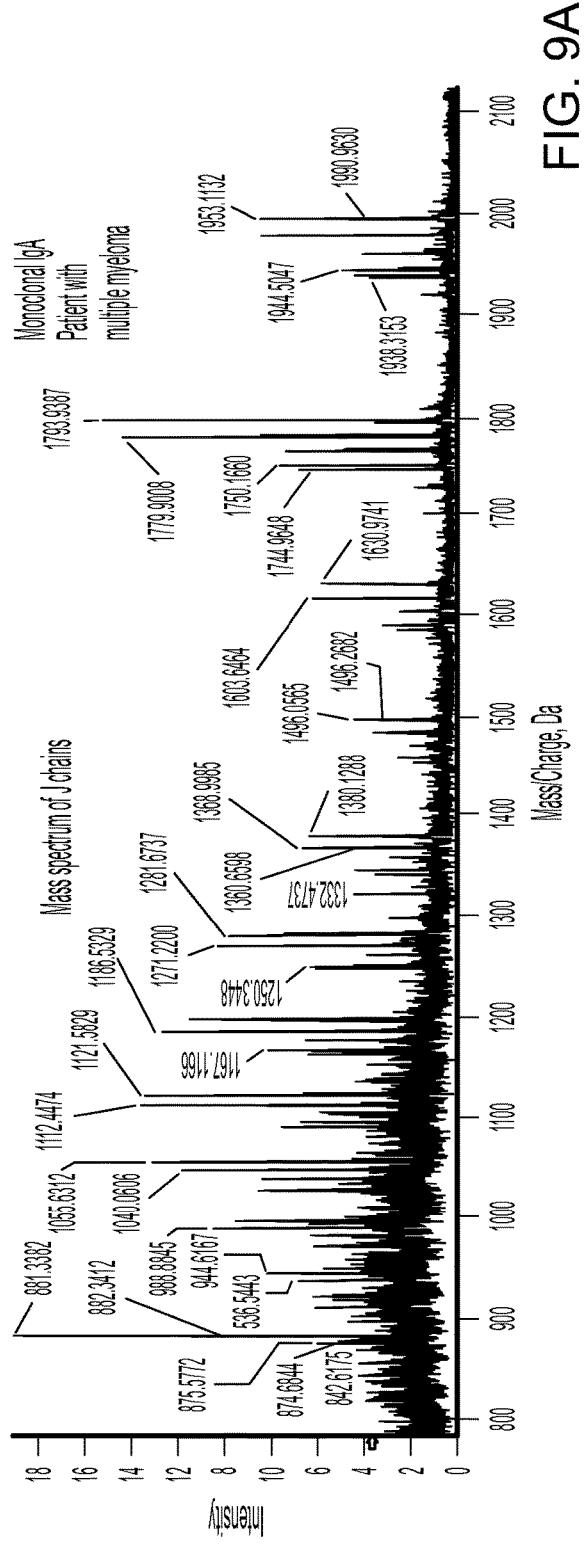
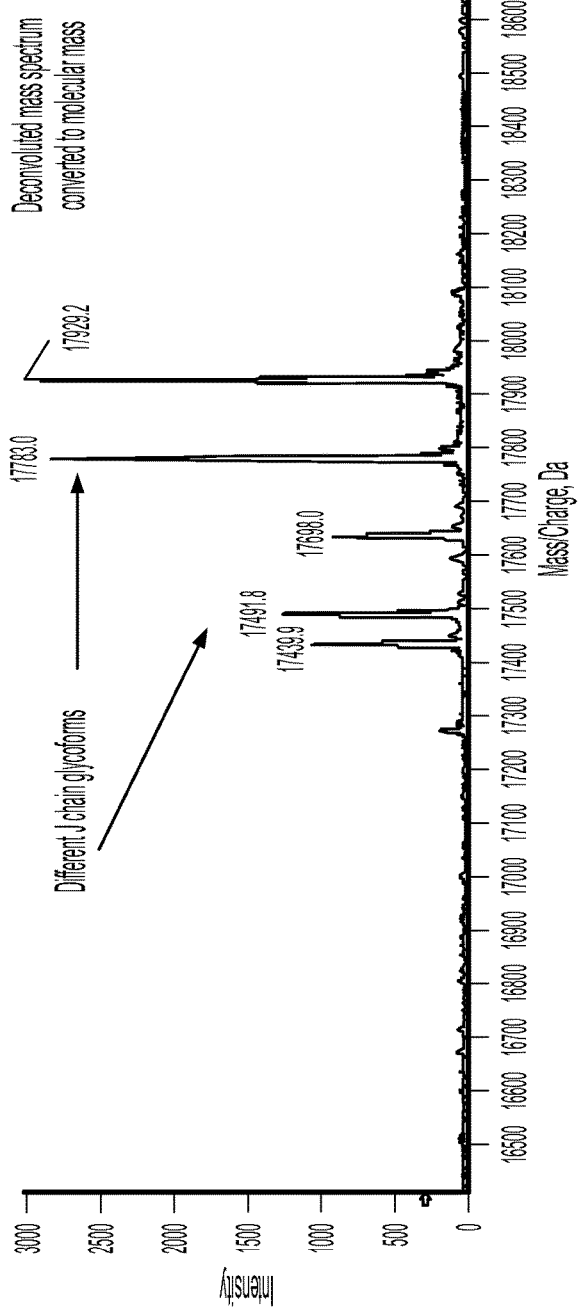
FIG. 9A
FIG. 9B

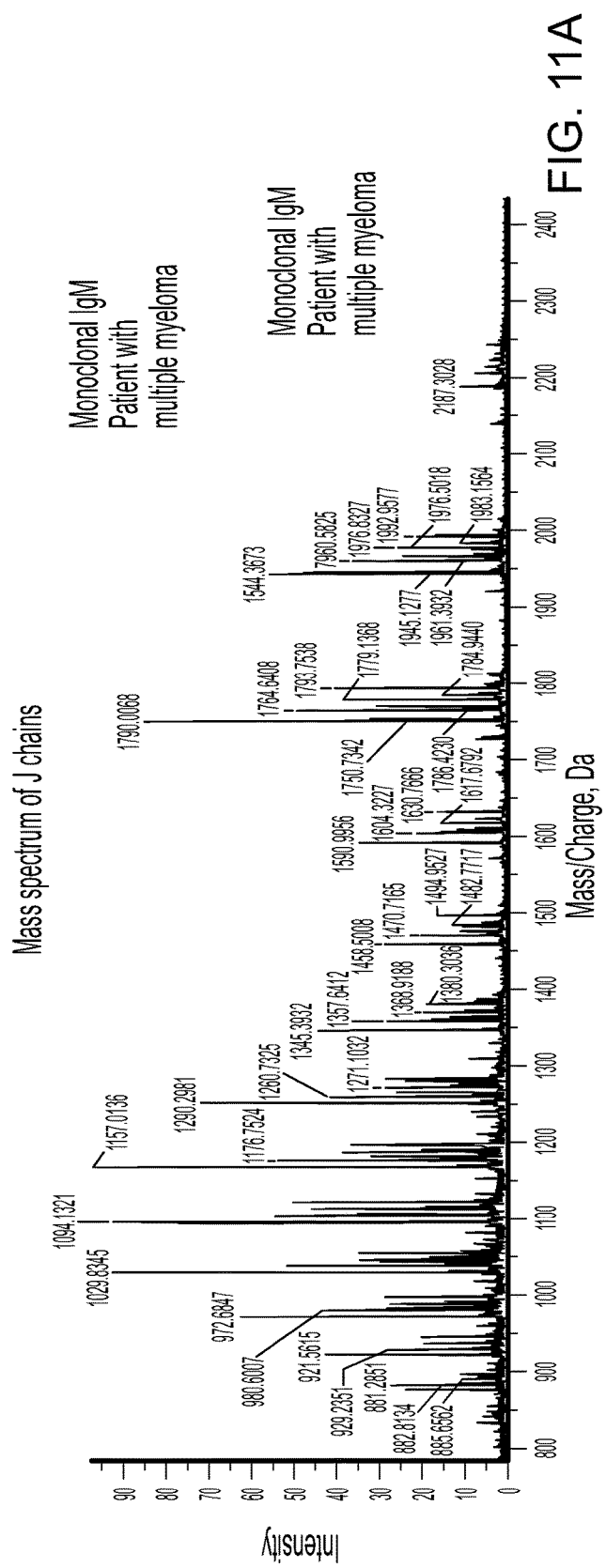
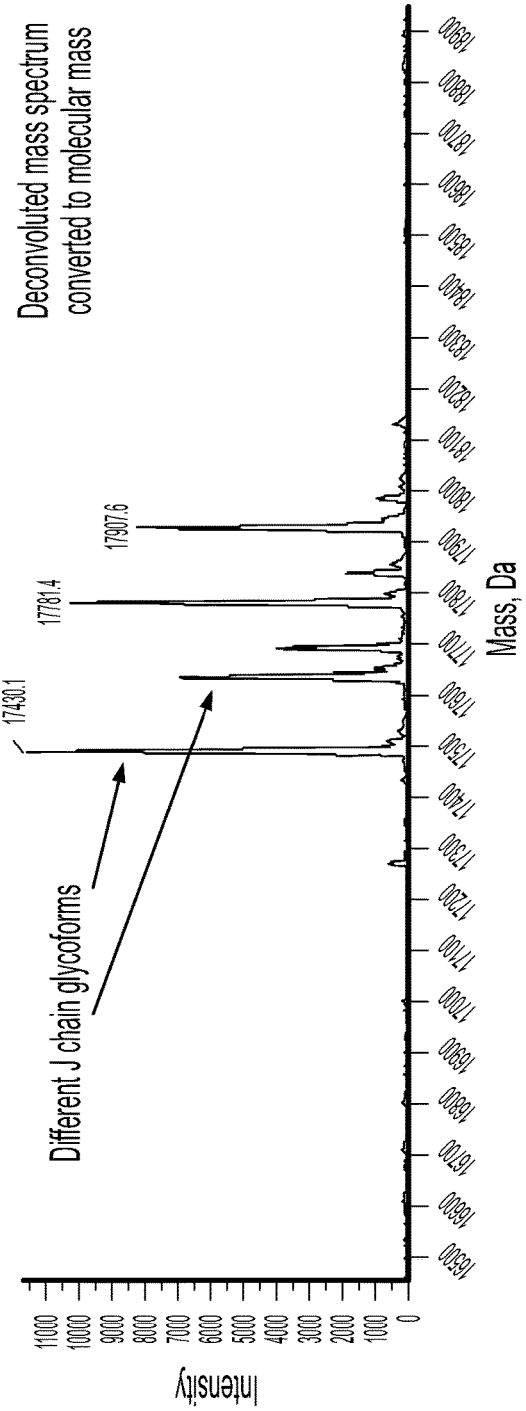
FIG. 11A
FIG. 11B

SEQUENCE LISTING

```
<160> NUMBER OF SEQ ID NOS: 2

<210> SEQ ID NO 1
<211> LENGTH: 137
<212> TYPE: PRT
<213> ORGANISM: Homo sapiens

<400> SEQUENCE: 1

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
                35                  40                  45

Asn Ile Ser Asp Pro Thr Ser Pro Leu Arg Thr Arg Phe Val Tyr His
        50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
            115                 120                 125

Leu Thr Pro Asp Ala Cys Tyr Pro Asp
    130                 135

<210> SEQ ID NO 2
<211> LENGTH: 9
<212> TYPE: PRT
<213> ORGANISM: Homo sapiens

<400> SEQUENCE: 2

Leu Thr Pro Asp Ala Cys Tyr Pro Asp
1               5
```

IDENTIFICATION AND MONITORING OF IMMUNOGLOBULIN J CHAINS

CROSS-REFERENCE TO RELATED APPLICATIONS

This application is a National Stage application under 35 U.S.C. § 371 of International Application No. PCT/US2018/050847, having an International Filing Date of Sep. 13, 2018, which claims the benefit of U.S. Patent Application Ser. No. 62/558,023, filed on Sep. 13, 2017. The disclosure of the prior application is considered part of (and is incorporated by reference in) the disclosure of this application.

BACKGROUND

1. Technical Field

This document relates to materials and methods for identifying and quantifying immunoglobulin J chains in a sample, such as a biological sample, using mass spectrometry techniques. In some cases, identification and quantification of the J chain can be used to identify and quantify IgA immunoglobulin dimers and/or IgM immunoglobulin pentamers.

2. Background Information

Human immunoglobulins contain two identical heavy chain polypeptides and two identical light chain polypeptides bound together by disulfide bonds. There are 2 different light chain isotypes (kappa and lambda) while there are 5 different heavy chain isotypes (IgG, IgA, IgM, IgD, and IgE). Each isotype has a unique amino acid sequence and set of post-translational modifications that are used to identify them.

A unique feature of immunoglobulins IgA and IgM is their ability to form multimers. In circulation IgA typically exists as a combination of monomers and dimers while IgM exists as a pentamer. IgA and IgM multimers form by connection through the J chain protein.

SUMMARY

This document provides materials and methods for identifying and quantifying immunoglobulin J chains in a sample, such as a biological sample, using mass spectrometry (MS) techniques. For example, the materials and methods provided herein can be used to identify and quantify J chains. In some cases, identification and quantification of the J chain can be used to identify and quantify multimeric IgA immunoglobulins (e.g., IgA dimers) and/or multimeric IgM immunoglobulins (e.g., IgM pentamers). For example, the materials and methods provided herein can be used to identify and quantify posttranslational modifications (e.g., glycosylation) on the J chain.

As demonstrated herein, MS can be used to analyze polyclonal and monoclonal IgA and IgM serum samples to obtain a comprehensive analysis of the J chain. For example, MS can be used to identify and quantify the J chain associated multimeric IgA immunoglobulins (e.g., IgA dimers) and/or multimeric IgM immunoglobulins (e.g., IgM pentamers). Further, MS also can be used to identify post-translational modifications on the J chain such as glycosylation. Notably, the methods described herein can be done without the need for additional instrumentation and/or J chain specific reagents. Having to the ability to identify and quantify the J chain associated with multimeric IgA immunoglobulins (e.g., IgA dimers) and/or multimeric IgM immunoglobulins (e.g., IgM pentamers), in a single assay, provides a unique and unrealized diagnostic tool to aid immunologists in monitoring a patient's immune system. For example, the J chain is associated with secretion, and accordingly, identifying and quantifying the J chain associated with multimeric IgA immunoglobulins and/or multimeric IgM immunoglobulins (e.g., IgA dimers and/or IgM pentamers from a patient serum sample) can be used to determine the amount of secretory IgA and/or IgM in a patient.

In general, one aspect of this document features a method for identifying J chains in a sample. The method includes, or consists essentially of, providing a sample comprising immunoglobulins, immunopurifying IgA immunoglobulins and/or IgM immunoglobulins from the sample, subjecting the immunopurified immunoglobulins to a MS technique to obtain a mass spectrum of the sample, and identifying the presence of J chains based on the multiply charged ion peaks in the spectrum corresponding to the J chains. The immunoglobulins can be intact (e.g., not fragmented) during the MS technique. The sample can be a biological sample (e.g., a biological fluid). The biological fluid can be blood, serum, plasma, urine, lachrymal fluid, or saliva. The biological fluid can be serum. The MS technique can include a liquid chromatography-mass spectrometry (LC-MS) technique. The MS technique can be electrospray ionization mass spectrometry (ESI-MS). The ESI-MS technique can include a quadrupole time-of-flight (TOF) mass spectrometer. The J chains can include a post-translational modification (e.g., glycosylation). The J chains can lack a post-translational modification. The immunopurifying can include using a non-human antibody (e.g., a camelid antibody, a cartilaginous fish antibody, llama, sheep, goat, rabbit, or a mouse antibody). The non-human antibody can be a camelid antibody. The antibody can be a single domain antibody fragment. The single domain antibody fragment can be derived from a camelid antibody.

In another aspect, this document features a method for quantifying the J chains in a sample. The method includes, or consists essentially of, providing a sample comprising immunoglobulins, immunopurifying IgA immunoglobulins and/or IgM immunoglobulins from the sample, subjecting the immunopurified immunoglobulins to a MS technique to obtain a mass spectrum of the sample, identifying the presence of J chains based on the multiply charged ion peaks in the spectrum corresponding to the J chains, and converting the peak area of the identified peaks to a molecular mass to quantify the J chains in the sample. The method also can include immunopurifying IgA from the sample, where the immunopurifying includes using an anti-human IgA antibody. The method also can include immunopurifying IgM from the sample, where the immunopurifying can include using an anti-human IgM antibody. The immunopurifying can include using a non-human antibody (e.g., a camelid antibody, a cartilaginous fish antibody, llama, sheep, goat, rabbit, or a mouse antibody). The non-human antibody can be a camelid antibody. The antibody can be a single domain antibody fragment. The single domain antibody fragment can be derived from a camelid antibody. The method also can include immunopurifying IgA immunoglobulins from the sample, and further include quantifying the IgA immunoglobulins. The IgA immunoglobulins can be multimeric IgA immunoglobulins. The quantifying can include determining the ratio of J chains to IgA immunoglobulins. The method also can include immunopurifying IgM immunoglobulins from the sample, and further include quantifying the IgM immunoglobulins. The IgM immunoglobulins can be multimeric IgM immunoglobulins. The quantifying can include determining the ratio of J chains to IgM immunoglobulins. The immunoglobulins can be intact (e.g., not fragmented) during the MS technique. The sample can be a biological sample (e.g., a biological fluid). The biological fluid can be blood, serum, plasma, urine, lachrymal fluid, or saliva. The biological fluid can be serum. The MS technique can include a liquid chromatography-mass spectrometry (LC-MS) technique. The MS technique can be electrospray ionization mass spectrometry (ESI-MS). The ESI-MS technique can include a quadrupole time-of-flight (TOF) mass spectrometer. The J chains can include a post-translational modification (e.g., glycosylation). The J chains can lack a post-translational modification.

In another aspect, this document features a method for diagnosing a disorder in a patient, where the disorder can be associated with abnormal production of IgA immunoglobulins and/or IgM immunoglobulins. The method includes, or consists essentially of, providing a sample comprising immunoglobulins from said patient, immunopurifying said IgA immunoglobulins and/or said IgM immunoglobulins from the sample, subjecting the immunopurified immunoglobulins to a MS technique to obtain a mass spectrum of the sample, identifying the presence of J chains based on the multiply charged ion peaks in the spectrum corresponding to the J chains, determining the ratio of J chains to IgA immunoglobulins and/or the ratio of J chains to IgM immunoglobulins in the sample, and comparing the ratio to a reference value. The disorder can be multiple myeloma, asymptomatic or smoldering multiple myeloma, solitary plasmacytoma, monoclonal gammopathy of undetermined significance, B-cell chronic lymphocytic leukemia, Waldenstrom macrogloblinemia, non-secretory myeloma, selective IgA deficiency, selective IgM deficiency, celiac disease, IgA nephropathy, autoimmune disorders, or a neurologic disease. The patient can be a mammal (e.g., a human). The immunopurifying can include using a non-human antibody (e.g., a camelid antibody, a cartilaginous fish antibody, llama, sheep, goat, rabbit, or a mouse antibody). The non-human antibody can be a camelid antibody. The non-human antibody can be a single domain antibody fragment. The single domain antibody fragment can be derived from a camelid antibody. The immunoglobulins can be intact (e.g., not fragmented) during the MS technique. The sample can be a biological sample (e.g., a biological fluid). The biological fluid can be blood, serum, plasma, urine, lachrymal fluid, or saliva. The biological fluid can be serum. The MS technique can include a liquid chromatography-mass spectrometry (LC-MS) technique. The MS technique can be electrospray ionization mass spectrometry (ESI-MS). The ESI-MS technique can include a quadrupole time-of-flight (TOF) mass spectrometer.

In another aspect, this document features a method for treating a disorder in a patient, where the disorder can be associated with abnormal production of IgA immunoglobulins and/or IgM immunoglobulins. The method includes, or consists essentially of, identifying the patient as having said disorder by providing a sample comprising immunoglobulins from said patient, immunopurifying IgA immunoglobulins and/or IgM immunoglobulins from the sample, subjecting the immunopurified immunoglobulins to a MS technique to obtain a mass spectrum of the sample, identifying the presence of J chains based on the multiply charged ion peaks in the spectrum corresponding to the J chains, determining the ratio of J chains to IgA immunoglobulins and/or the ratio of J chains to IgM immunoglobulins in the sample; comparing the ratio to a reference value; and administering to said patient a therapeutic agent to treat said disorder. The method also can include performing a plasma exchange or a stem cell transplant. The disorder can be multiple myeloma, asymptomatic or smoldering multiple myeloma, solitary plasmacytoma, monoclonal gammopathy of undetermined significance, B-cell chronic lymphocytic leukemia, Waldenstrom macrogloblinemia, non-secretory myeloma, selective IgA deficiency, selective IgM deficiency, celiac disease, IgA nephropathy, autoimmune disorders, or a neurologic disease. The patient can be a mammal (e.g., a human). The immunopurifying can include using a non-human antibody (e.g., a camelid antibody, a cartilaginous fish antibody, llama, sheep, goat, rabbit, or a mouse antibody). The non-human antibody can be a camelid antibody. The non-human antibody can be a single domain antibody fragment. The single domain antibody fragment can be derived from a camelid antibody. The immunoglobulins can be intact (e.g., not fragmented) during the MS technique. The sample can be a biological sample (e.g., a biological fluid). The biological fluid can be blood, serum, plasma, urine, lachrymal fluid, or saliva. The biological fluid can be serum. The MS technique can include a liquid chromatography-mass spectrometry (LC-MS) technique. The MS technique can be electrospray ionization mass spectrometry (ESI-MS). The ESI-MS technique can include a quadrupole time-of-flight (TOF) mass spectrometer.

In another aspect, this document features a method for monitoring a treatment of a disorder in a patient, where the disorder can be associated with abnormal production of IgA immunoglobulins and/or IgM immunoglobulins. The method includes, or consists essentially of, providing an initial sample comprising immunoglobulins from the patient, where the initial sample can be obtained from the patient prior to the treatment, providing one or more secondary samples comprising immunoglobulins, where the one or more secondary samples are obtained from the patient during the treatment, after the treatment, or both, immunopurifying IgA immunoglobulins and/or IgM immunoglobulins from the samples, subjecting the immunopurified immunoglobulins to a MS technique to obtain a mass spectrum of the samples, identifying the presence of J chains in said samples based on the multiply charged ion peaks in the spectrum corresponding to the J chains, determining the ratio of J chains to IgA immunoglobulins and/or the ratio of J chains to IgM immunoglobulins in the samples, and comparing the ratios from the initial sample and the one or more secondary samples. The disorder can be multiple myeloma, asymptomatic or smoldering multiple myeloma, solitary plasmacytoma, monoclonal gammopathy of undetermined significance, B-cell chronic lymphocytic leukemia, Waldenstrom macrogloblinemia, non-secretory myeloma, selective IgA deficiency, selective IgM deficiency, celiac disease, IgA nephropathy, autoimmune disorders, or a neurologic disease. The patient can be a mammal (e.g., a human). The immunopurifying can include using a non-human antibody (e.g., a camelid antibody, a cartilaginous fish antibody, llama, sheep, goat, rabbit, or a mouse antibody). The non-human antibody can be a camelid antibody. The non-human antibody can be a single domain antibody fragment. The single domain antibody fragment can be derived from a camelid antibody. The immunoglobulins can be intact (e.g., not fragmented) during the MS technique. The sample can be a biological sample (e.g., a biological fluid). The biological fluid can be blood, serum, plasma, urine, lachrymal fluid, or saliva. The biological fluid can be serum. The MS technique can include a liquid chromatography-mass spectrometry (LC-MS) technique. The MS technique can be electrospray ionization mass spectrometry (ESI-MS). The ESI-MS technique can include a quadrupole time-of-flight (TOF) mass spectrometer.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 9A-9B contain MS spectra of different glycoforms of IgA J chains. A) A summed mass spectrum of J chains from the peaks in FIGS. 8B and 8C. B) A deconvoluted mass spectrum of J chains from the peaks in FIGS. 8B and 8C.

FIGS. 11A-11B contain MS spectra of different glycoforms of IgM J chains. A) A summed mass spectrum of J chains from the peaks in FIGS. 8B and 8C. B) A deconvoluted mass spectrum of J chains from the peaks in FIGS. 8B and 8C.

DETAILED DESCRIPTION

Figure 1:
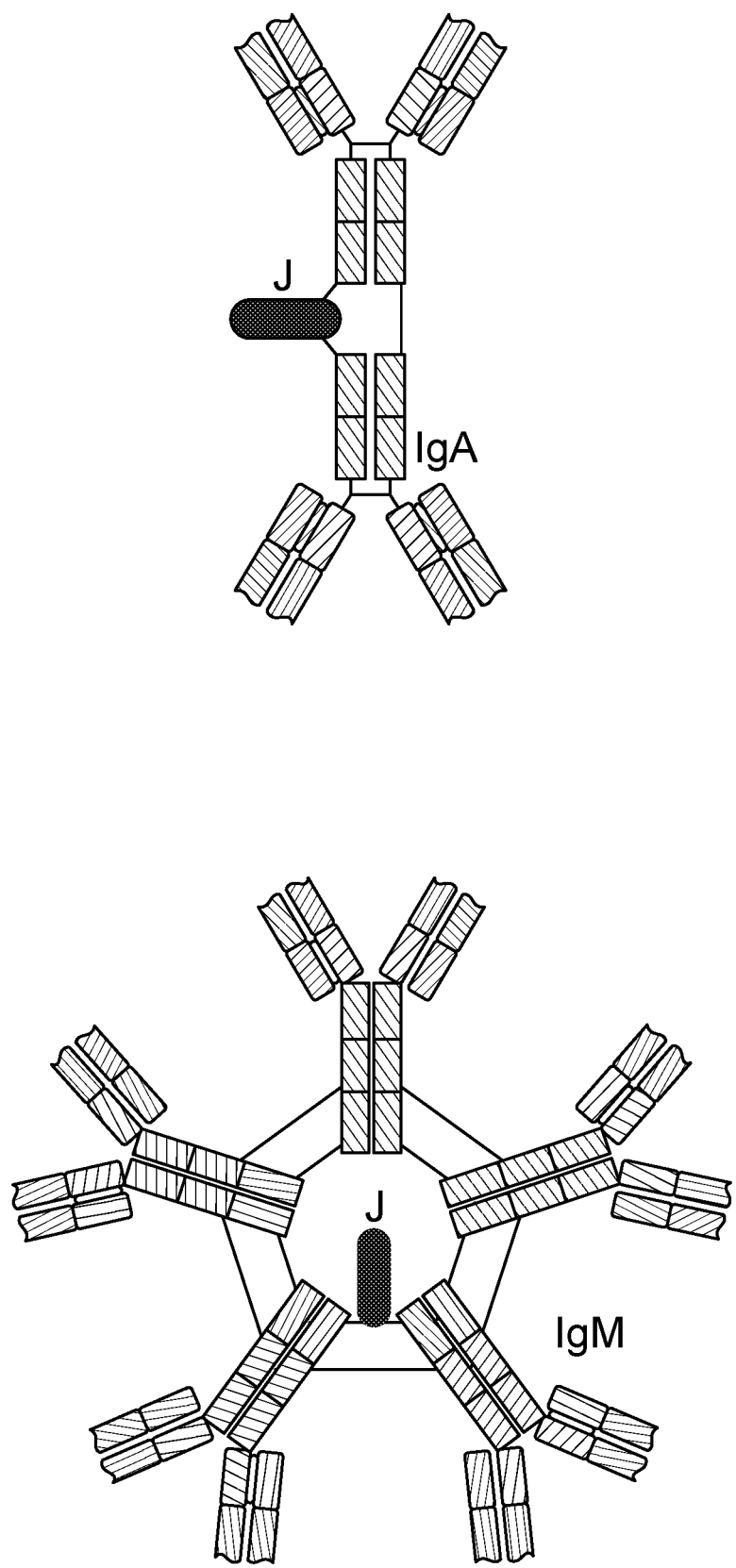
FIG. 1 is a schematic model of IgA multimers and IgM multimers. The J chain is shown as an oval that completes the coupling of the multimeric forms of IgA and IgM via the blue colored fragment crystallizable region (Fc region) of the heavy chain. The red lines represent disulfide bonds that are also formed in addition to the J chain binding to IgA and IgM.

This document provides methods and materials for identifying and quantifying immunoglobulin J chains and/or identifying the presence or absence, quantity, and/or glycoform(s) of the J chain in a sample using MS techniques. For example, the materials and methods provided herein can be used to identify and quantify the J chain associated with IgA multimers and IgM multimers. In some cases, identification and quantification of the J chain can be used to identify and quantify multimeric IgA immunoglobulins (e.g., IgA dimers) and/or multimeric IgM immunoglobulins (e.g., IgM pentamers).

J chains described herein can be detected using MS. The speed, sensitivity, resolution, and robustness of MS make the present methods superior to gel electrophoresis for screening samples for the presence or absence, quantity, and/or glycoform(s) of J chains. A method described herein can include the use of a liquid chromatography MS (LC-MS). In some cases, electrospray ionization MS (ESI-MS) techniques can be used, for example, an electrospray ionization quadrupole time-of-flight MS (ESI-Q-TOF MS) technique. In some cases, a MS technique can be a top-down MS technique. The use of mass over charge (m/z), optionally with additional techniques, such as gel electrophoresis and/or peptide sequencing, provides a more direct assessment of the J chain because it can be used to determine the quantity of the intact J chain and the extent of J chain glycosylation in a single assay.

The methods described herein, also referred to as monoclonal immunoglobulin Rapid Accurate Mass Measurement (miRAMM), can be used to identify and quantify J chains in a sample (e.g., a serum sample) without the need for additional instrumentation or reagents specific to the J chain. The J chain can be identified in the purified sample by its molecular mass. The mean molecular mass for J chains is about 17.5 kDa (17,500 Da). Different J chain glycoforms can have a molecular mass of about 17,400 Da to about 17,900 Da. The presence or absence, quantity, and/or glycoform(s) of J chains can be determined by detecting a J chain amino acid sequence. An exemplary J chain can be a human J chain amino acid sequence as set forth below:

(SEQ ID NO: 1)
QEDERIVLVDNKCKCARITSRIIRSSEDPNEDIVERNIRIIVPLNNRENI

SDPTSPLRTRFVYHLSDLCKKCDPTEVELDNQIVTATQSNICDEDSATET

CYTYDRNKCYTAVVPLVYGGETKMVETALTPDACYPD.

In some cases, the methods described herein can detect a fragment (e.g., the C-terminus) of a J chain. For example, a J chain can include the amino acid sequence LTPDACYPD (SEQ ID NO:2).

In some cases, a J chain can lack posttranslational modifications (e.g., glycosylation).

In some cases, a J chain can include one or more posttranslational modifications (e.g., glycosylation). A glycosylated J chain can include any appropriate carbohydrate (e.g., deoxyhexose, hexose, N-acetylhexosamine, and sialic acid). A glycosylated J chain can include an N-linked carbohydrate. For example, a glycosylated J chain can include an N-linked carbohydrate at asparagine (N) 49.

The methods described herein can be used to identify and quantify J chains in a sample (e.g., a serum sample) without the need for additional instrumentation or reagents specific to the J chain. The identification and quantification of the J chain can be used to identify and quantify IgA and/or IgM immunoglobulins. For example, an abundance ratio index of intact J chain to intact polyclonal or monoclonal IgA and IgM can be used to determine the amount of multimeric IgA and IgM present in sample (e.g., a serum sample). Thus, the methods described herein provide the ability to identify and quantify the J chain, IgA immunoglobulins, and IgM immunoglobulins, all in the same assay. These methods are useful for screening biological samples for the presence or absence, quantity, and/or glycoform of the J chain, for identifying IgA and/or IgM gammopathies in a patient, for monitoring IgA and/or IgM in a patient, and/or for monitoring treatment of a disorder in a patient.

Samples and Sample Preparation

The materials and methods for identifying and quantifying J chains as described herein can include any appropriate sample. A sample can be any biological sample, such as a tissue (e.g., adipose, liver, kidney, heart, muscle, bone, or skin tissue) or biological fluid (e.g., blood, serum, plasma, urine, lachrymal fluid, or saliva). The sample can be from a patient that has immunoglobulins, which includes but is not limited to a mammal, e.g. a human, dog, cat, primate, rodent, pig, sheep, cow, horse, bird, reptile, or fish. A sample can also be a man-made reagent, such as a mixture of known composition or a control sample. In some cases, the sample is serum from a human patient.

A sample can be treated to remove components that could interfere with the MS technique. A variety of techniques known to those having skill in the art can be used based on the sample type. Solid and/or tissue samples can be ground and extracted to free the analytes of interest from interfering components. In such cases, a sample can be centrifuged, filtered, and/or subjected to chromatographic techniques to remove interfering components (e.g., cells or tissue fragments). In yet other cases, reagents known to precipitate or bind the interfering components can be added. For example, whole blood samples can be treated using conventional clotting techniques to remove red and white blood cells and platelets. A sample can be deproteinized. For example, a plasma sample can have serum proteins precipitated using conventional reagents such as acetonitrile, KOH, NaOH, or others known to those having ordinary skill in the art, optionally followed by centrifugation of the sample.

Immunoglobulins can be isolated from the samples or enriched (i.e. concentrated) in a sample using standard methods known in the art. Such methods include removing one or more non-immunoglobulin contaminants from a sample. In some cases, the samples can be enriched or purified using immunopurification, centrifugation, filtration, ultrafiltration, dialysis, ion exchange chromatography, size exclusion chromatography, protein A/G or avidin-streptavidin/biotin affinity purification, precipitation, gel electrophoresis, capillary electrophoresis, chemical fractionation (e.g., antibody purification kits, such as Melon Gel Purification), and aptamer techniques. For example, the immunoglobulins can be purified by chemical-based fractionation, e.g., Melon Gel Chromatography (Thermo Scientific), where Melon Gel resins bind to non-immunoglobulin proteins in a sample and allow immunoglobulins to be collected in the flow-through fraction; or by affinity purification, e.g., by Protein A, Protein G, Protein L, or streptavidin/biotin purification, where immunoglobulins are bound by those proteins at physiologic pH and then released from the proteins by lowering the pH. When serum, plasma, or whole blood samples are used, a sample, such as a 10-250 µl sample (e.g., a 50 µl sample), can be directly subjected to Melon Gel, Protein A, Protein G or Protein L purification. Size exclusion principles such as a TurboFlow column can also be employed to separate the non-immunoglobulin contaminants from a sample. When urine samples are used, a urine sample can be buffered, e.g., a 50 µl urine sample can be diluted first with 50 µl of 50 mM ammonium bicarbonate.

A sample can be subject to immunopurification prior to analysis by MS. In some cases, the sample can be immunoglobulin enriched. Immunopurification can result in enrichment of one or more immunoglobulins (e.g., IgA and/or IgM). For example, immunopurification can separate or enrich immunoglobulin IgA in a sample. For example, immunopurification can separate or enrich IgM in a sample. Immunopurification can involve contacting a sample containing the desired antigen with an affinity matrix including an antibody (e.g. single domain antibody fragments, also referred to as nanobodies) to the antigen covalently attached to a solid phase (e.g., beads such as agarose beads). Antigens in the sample become bound to the affinity matrix through an immunochemical bond. The affinity matrix is then washed to remove any unbound species. The antigen is then removed from the affinity matrix by altering the chemical composition of a solution in contact with the affinity matrix. The immunopurification may be conducted on a column containing the affinity matrix, in which case the solution is an eluent or in a batch process, in which case the affinity matrix is maintained as a suspension in the solution. In some cases, the antibody can be a labelled antibody (e.g. a biotinylated antibody) and a binding partner of the label (e.g., avidin and/or streptavidin) can be attached to the solid phase.

In some embodiments, single domain antibody fragments (SDAFs) with an affinity for immunoglobulins can be used in the immunopurification process. SDAFs can be derived from heavy chain antibodies of non-human sources (e.g., camelids, fish, llama, sheep, goat, rabbit, or mouse), heavy chain antibodies of human sources, and light chain antibodies of humans. SDAFs possess unique characteristics, such as low molecular weight, high physical-chemical stability, good water solubility, and the ability to bind antigens inaccessible to conventional antibodies. For example, IgA immunoglobulins can be immunopurified using anti-IgA camelid nanobodies. For example, IgM immunoglobulins can be immunopurified using anti-IgM camelid nanobodies.

In some embodiments, isolation of immunoglobulins can be performed with an entity other than a traditional antibody-which contains both heavy and light chains (such as those used in IFE and various known clinical immunoassays). Traditional antibodies contain heavy and/or light chains with masses that may overlap with the masses of the immunoglobulins in the sample of interest (e.g., human immunoglobulins). Therefore, these antibodies may interfere in the mass spectra of the patient's immunoglobulins. Single domain antibody fragments (SDAFs) may have masses ranging from 12,500-15,000 Da and, using the methods described herein, may carry a single charge thus generating a signal in the range of 12,500-15,000 m/z, which does not overlap with the signals generated by human heavy chains or light chains. The identification of human light chains and heavy chains by molecular mass can be done as described elsewhere (see, e.g., WO 2015/154052). Thus, in some embodiments, the use of specific isolation of IgA and/or IgM utilizing SDAFs, coupled with mass identification, results in a specific and sensitive method for the detection of J chains.

In some cases, the immunoglobulins (e.g., IgA and/or IgM) are substantially isolated. By "substantially isolated" is meant that the immunoglobulins are at least partially or substantially separated from the sample from which they were provided. Partial separation can include, for example, a sample enriched in the immunoglobulins. Substantial separation can include samples containing at least about 10%, at least about 20%, at least about 30%, at least about 40%, at least about 50%, at least about 60%, at least about 70%, at least about 80%, at least about 90%, at least about 95%, at least about 97%, or at least about 99% by weight of the immunoglobulin.

In some cases, intact immunoglobulins can be further processed to decouple the light chains in a total immunoglobulin sample from the heavy chain immunoglobulins. Decoupling can be achieved by treating the total immunoglobulins with a reducing agent, such as DTT (2,3 dihydroxybutane-1,4-dithiol), DTE (2,3 dihydroxybutane-1,4-dithiol), thioglycolate, cysteine, sulfites, bisulfites, sulfides, bisulfides, TCEP (tris(2-carboxyethyl)phosphine), 2-mercaptoethanol, and salt forms thereof. In some cases, the reducing step is performed at elevated temperature, e.g., in a range from about 30° C. to about 65° C., such as about 55° C., in order to denature the proteins. In some cases, the sample is further treated, e.g., by modifying the pH of the sample or buffering the sample. In some cases, the sample can be acidified. In some cases, the sample can be neutralized (e.g., by the addition of a base such as bicarbonate).

In some cases, the antigen binding fragments (Fab) of immunoglobulins can be cleaved from the intact immunoglobulins using proteases such as pepsin. Excess reagents and salts can be removed from the samples using methods known to those having ordinary skill in the art.

Mass Spectrometry Methods

The materials and methods for identifying and quantifying J chains as described herein can include any appropriate MS technique. After sample preparation, a sample can be subjected to a MS technique, either directly or after separation on a high performance liquid chromatography column (HPLC). In some cases, LC-MS can be used to analyze the mass spectrum of the ions. For example, the method can be used to identify multiply charged ions (e.g., the +1 ions, +2 ions, +3 ions, +4 ions, +5 ions, +6 ions, +7 ions, +8 ions, +9 ions, +10 ions, +11 ions, +12 ions, +13 ions, +14 ions, +15 ions, +16 ions, +17 ions, +18 ions, +19 ions, +20 ions, +21 ions, and +22 ions), resulting from the J chains in the sample. In some cases, the +16 charged ion is identified and used for further analysis. In some cases, the samples are not fragmented during the MS technique. LC-MS is an analytical technique that combines the physical separation capabilities of liquid chromatography with the mass analysis capabilities of MS, and is suitable for detection and potential identification of chemicals in a complex mixture. Any LC-MS instrument can be used, e.g., the ABSciex 5600 Mass Spectrometer. In some cases, microflowLC-MS can be utilized. Any suitable microflow instrument can be used, e.g., the Eksigent Ekspert 200 microLC. The ion mass spectrum can be analyzed for one or more peaks corresponding to one or more J chains in the sample. For example, one or more ion peaks, e.g., a +16 ion peak, can be examined to identify and monitor the J chains in the sample.

In some cases, ESI-Q-TOF MS can be used to analyze the mass spectrum of a sample, e.g., the mass spectrum of the +16 charge state of the J chain in the sample. ESI MS is a useful technique for producing ions from macromolecules because it overcomes the propensity of these molecules to fragment when ionized. In addition, ESI often produces multiply charged ions, effectively extending the mass range of the analyzer to accommodate the orders of magnitude observed in proteins and other biological molecules. A quadrupole mass analyzer (Q) consists of four cylindrical rods, set parallel to each other. In a quadrupole mass spectrometer, the quadrupole is the component of the instrument responsible for filtering sample ions based on their mass-to-charge ratio (m/z). The time-of-flight (TOF) analyzer uses an electric field to accelerate the ions through the same potential, and then measures the time they take to reach the detector. If the particles all have the same charge, the kinetic energies are identical, and their velocities depend only on their masses. Lighter ions reach the detector first. Any ESI-Q-TOF mass spectrometer can be used, e.g., the ABSciex TripleTOF 5600 quadrupole TOF mass spectrometer. The mass spectrum, e.g., the mass spectrum of multiply charged intact J chain, light chain, and/or heavy chain polypeptide ions, can be analyzed to identify one or more peaks at an appropriate mass/charge expected for the chain. For example, for the J chain, the peaks (e.g., fragment ion peaks) can occur at about 100-2500 m/z. In some cases, the peaks can occur at about 150-1200 m/z (e.g., about 200-1000 m/z for the +16 ion).

The multiply charged ion peaks can be converted to a molecular mass using known techniques. For example, multiply charged ion peak centroids can be used to calculate average molecular mass and the peak area value used for quantification is supplied by a software package. Specifically, multiple ion deconvolution can be performed using the Bayesian Protein Reconstruct software package in the BioAnalyst companion software package in ABSCIEX Analyst TF 1.6. Deconvoluted and multiply charged ions can also be manually integrated using the Manual Integration 33 script in Analyst TF. Providing the molecular mass for the J chain in the sample facilitates sequencing and identification of the J chain in the sample. For example, the methods provided herein can be used to identify and quantify J chains in the sample. In addition, the methods provided herein can be used to compare the relative abundance of the J chains as compared to a control or reference sample. As described herein, the J chain can include the C-terminal amino acid sequence LTPDACYPD (SEQ ID NO:2). The abundance of this J chain sequence can be indicative of the abundance of multimeric IgA and IgM immunoglobulins and therefore is a useful tool for diagnosing and monitoring patients with an IgA gammopathy and/or IgM gammopathy.

In some cases, matrix assisted laser adsorption ionization—time-of-flight (MALDI-TOF) MS can be used to analyze the mass spectrum of a sample. MALDI-TOF MS identifies proteins and peptides as mass charge (m/z) spectral peaks. Further, the inherent resolution of MALDI-TOF MS allows assays to be devised using multiple affinity ligands to selectively purify/concentrate and then analyze multiple proteins in a single assay.

Methods for Assessing J Chains

The materials and methods provided herein can be used for identifying and monitoring J chains. In some cases, the methods provided herein can be used to determine the presence or absence, quantity, and/or glycoform of the J chain. For example, the presence or absence, quantity, and/or glycoform of the J chain can be used for identifying IgA and/or IgM gammopathies in a patient, for monitoring IgA and/or IgM in a patient, and/or for monitoring treatment of a disorder in a patient. For example, an abundance ratio of intact J chain to intact polyclonal or monoclonal IgA or IgM can be used to determine the amount of multimeric IgA or IgM.

The MS based methods disclosed herein can be used to screen a sample (e.g., a biological sample) for the presence, absence, or amount of J chains. In some cases, the MS based methods disclosed herein can be used for detecting J chains in a sample from a patient. In some cases, the MS based methods disclosed herein can be used for detecting IgA immunoglobulins and/or IgM immunoglobulins in a patient. An abundance ratio of intact J chain to intact polyclonal or monoclonal IgA and/or IgM can be used to determine the amount of multimeric IgA immunoglobulins and/or IgM immunoglobulins. For example, the presence of a single J chain can indicate the presence of a single intact IgA dimer (e.g., in an immunopurified IgA sample) or the presence of a single intact IgM pentamer (e.g., in an immunopurified IgM sample). In some cases, the MS based methods disclosed herein can be used for diagnosing and/or treating a patient having an IgA gammopathy and/or IgM gammopathy.

The MS based methods disclosed herein can include subjecting a sample having one or more immunoglobulins to a MS assay. The sample can be pretreated to isolate or enrich immunoglobulins present in the sample. The immunoglobulin light chains can be decoupled from the immunoglobulin heavy chains prior to the MS analysis. The spectrum obtained from the assay can then be used to identify J chains in the sample. In some cases, the abundance (e.g., quantity) of J chains can be determined by converting the peak areas of one or more of the identified peaks into a molecular mass.

The ratios, relative abundance, and/or glycoform of the J chains can be used to diagnose various disorders associated with abnormal production of IgA and/or IgM including, but not limited to, polyclonal gammopathies (e.g., IgA gammopathies and/or IgM gammopathies), autoimmune disorders, infectious disorders, and/or inflammatory disorders. A disorder can be chronic or acute (e.g., due to infection). When the disorder is a gammopathy, the gammopathy can include an overproduction of immunoglobulins or a deficiency of immunoglobulins. When the disorder is a gammopathy, the gammopathy can be a monoclonal gammopathy or a polyclonal gammopathy. Examples of disorders associated with abnormal production of IgA and/or IgM include, without limitation, multiple myeloma, asymptomatic or smoldering multiple myeloma, solitary plasmacytoma, monoclonal gammopathy of undetermined significance, B-cell leukemia (e.g., B-cell chronic lymphocytic leukemia), Waldenstrom macrogloblinemia, non-secretory myeloma, selective IgA deficiency, selective IgM deficiency, celiac disease, IgA nephropathy, autoimmune disorders, and neurologic diseases.

In some cases, the ratios and relative abundance of the J chains can be compared to a reference value or a control sample. For example, a reference value can be a relative abundance of J chains, IgA, and/or IgM in a healthy patient (e.g., a healthy human). For example, a control sample can be a sample (e.g., serum) obtained from one or more healthy patients (e.g., healthy humans).

In some cases, the methods provided herein can be used to confirm a diagnosis made by current methods such as gel electrophoresis. For example, if a negative result is obtained from gel electrophoresis, the present methods can be used as a secondary test to confirm or counter such results. In some cases, the diagnosis provided herein can be confirmed using such standard methods.

In some cases, the methods provided herein can be used for treating a patient having a gammopathy. For example, after diagnosing the subject as having a gammopathy as described herein (e.g., based on the presence or absence, quantity, and/or glycoform of the J chain), the methods can include administering to the patient a therapeutic agent to treat the gammopathy (e.g., a therapeutically effective amount) and/or performing a treatment (e.g., a plasma exchange or a stem cell transplant). The therapeutic agent can be any appropriate therapeutic agent. For example, when the gammopathy is a monoclonal gammopathy of undetermined significance, the therapeutic agent can be a bisphosphonate. Non-limiting examples of bisphosphonates include alendronate (e.g., BINOSTO®, FOSAMAX®, risedronate (e.g., ACTONEL®, ATELVIA®), ibandronate (e.g., BONIVA®) and zoledronic acid (e.g., RECLAST®, ZOMETA®). For example, when the gammopathy is a B-cell chronic lymphocytic leukemia, the therapeutic agent can be chlorambucil, fludarabine (e.g., FLUDARA®), cyclophosphamide (e.g., CYTOXAN®), bendamustine, cyclophosphamide, doxorubicin, vincristine (e.g., ONCOVIN®), prednisonea, chlorambucil, obinutuzumab, ofatumumab, pentostatin (e.g., NIPENT®), alemtuzumab (e.g., CAMPATH®), fludarabine, a monoclonal antibody (e.g., rituximab), or any combinations thereof. For example, when the gammopathy is Waldenstroms macrogloblinemia, the therapeutic agent can be bortezomib, thalidomide, fludarabine, dexamethasone, chlorambucil, cyclophosphamide, doxorubicin, vincristine, prednisone, a monoclonal antibody (e.g., rituximab), a purine nucleoside analog (e.g., cladribine), ibrutinib, or any combinations thereof. For example, when the gammopathy is a non-secretory myeloma, the therapeutic agent can be thalidomide, bortezomib, lenalidomide, carfilzomib, pomalidomide, or any combinations thereof. In some cases, after diagnosing the subject as having a gammopathy, the method can include administering to the subject a therapeutically effective amount of a therapeutic agent to treat the gammopathy and one or more of a plasma exchange and a stem cell transplant (e.g., an autologous peripheral blood stem cell transplantation).

In some cases, the methods provided herein can also be used for monitoring a patient. For example, the MS based methods disclosed herein can be used for monitoring a IgA gammopathy and/or a IgM gammopathy in a patient. The MS based methods disclosed herein can include providing a first sample and a second sample of the subject. For example, the MS based methods disclosed herein can include providing a first sample of the subject before the treatment and a second sample of the subject during or after the treatment. The first and second samples can be pretreated to isolate or enrich immunoglobulins present in the first and second samples. The immunoglobulin light chains in the first and second samples can be decoupled from the immunoglobulin heavy chains prior to the MS analysis. The spectrum obtained from the assay can then be used to identify J chains in the first and second samples. In some cases, the relative abundance of J chains in the first and second samples can be determined by converting the peak areas of one or more of the identified peaks into a molecular mass. The presence or absence of J chains can be determined in the first and second samples. A decrease (or loss) of the amount of J chains indicates that the IgA gammopathy and/or IgM gammopathy in the patient has been reduced (or eliminated); while an increase in the amount of J chains indicates that the IgA gammopathy and/or IgM gammopathy in the patient has increased. In cases where a first sample of the subject is before the treatment and a second sample of the subject is during or after the treatment, the presence or absence of J chains is determined before and after the treatment and compared. A decrease (or loss) of the amount of J chains indicates that the treatment may be effective for the subject; while an increase or no change in the amount of J chains indicates that the treatment may be ineffective for the subject. For example, the amount of J chains in a first sample and in a second sample can be determined, and the amount of J chains in the first sample can be compared to the amount of J chains and the second sample. For example, the concentration of J chains in a first sample and in a second sample can be determined, and the concentration of J chains in the first sample can be compared to the amount of J chains and the second sample.

The invention will be further described in the following examples, which do not limit the scope of the invention described in the claims.

EXAMPLES

Example 1: Mass Spectrometry to Identify J Chain Fragments in Patient Serum

IgA and IgM immunoglobulins to form multimers as shown in FIG. 1. In circulation IgA typically exists as a combination of monomers and dimers while IgM exists as a pentamer. In order for multimers of both IgA and IgM to form they must be connected by a 17.5 kDa protein called the J chain (see, e.g., FIG. 1).

Methods

A volume of 50 µL of normal control pooled serum was added to 20 µL of anti-IgA or anti-IgM nanobody beads. The serum was allowed to incubate with the nanobody beads for 45 minutes. The beads were washed with 1 mL of PBS 3 times each time removing and discarding the supernatant. The beads were then washed with water 1 time. The water was removed and 50 µL of 5% acetic acid containing 50 mM TCEP was added to the beads to elute the purified immunoglobulins. This elute was then analyzed by microflow LC-ESI-Q-TOF MS using a SCIEX 5600 mass spectrometer.

Results

Figure 2A:
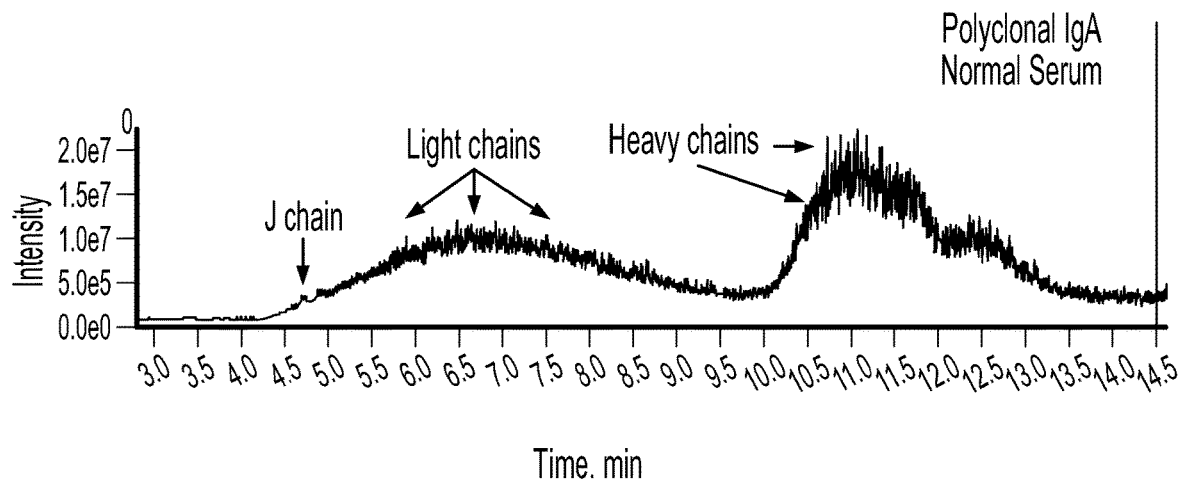
FIGS. 2A-2C contain MS spectra of polyclonal IgA. A) A total ion chromatogram (TIC) of polyclonal IgA in a pooled sample of normal human serum. B) An extracted TIC specific for peaks from a glycosylated J chain (glycoform 2). C) An extracted TIC specific for peaks from a glycosylated J chain (glycoform 1).
Figure 2B:
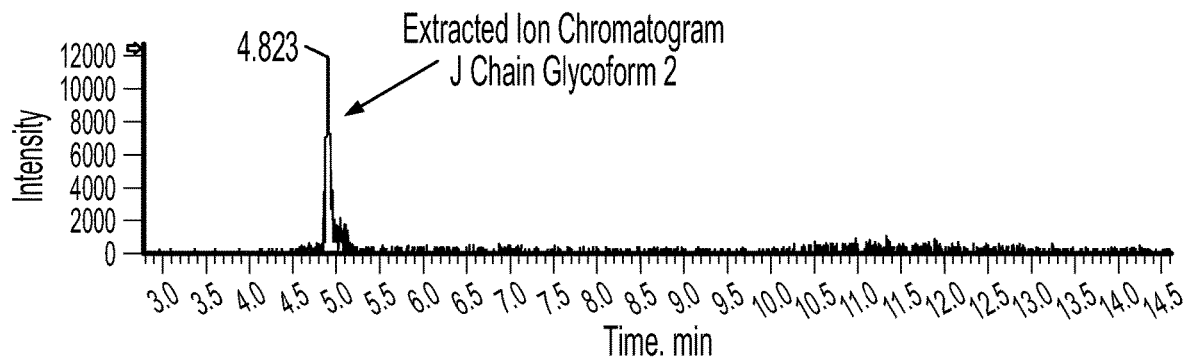
Figure 2C:
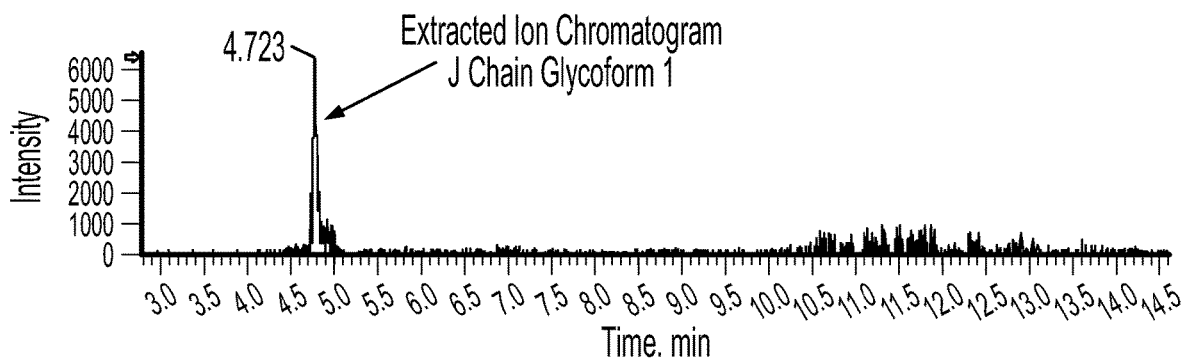
Figures 3A, 3B:
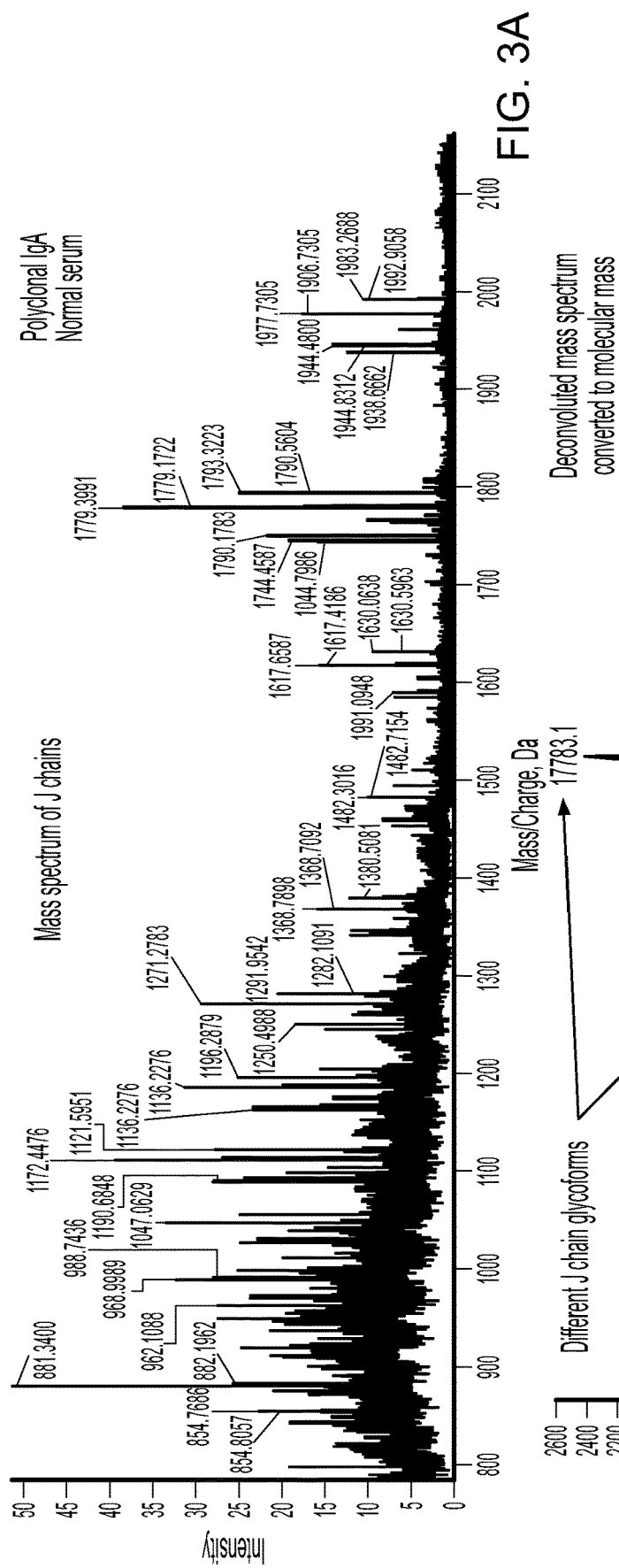
FIGS. 3A-3B contain MS spectra of different glycoforms of IgA J chains. A) A summed mass spectrum of J chains from the peaks in FIGS. 2B and 2C. B) A deconvoluted mass spectrum of J chains from the peaks in FIGS. 2B and 2C.

IgA was purified using camelid nanobody beads from normal pooled serum and subjected to MS (FIG. 2A). Extracted ion chromatograms specific for peaks from the J chain (FIGS. 2B and 2C) show the relative abundance of the J chain compared to all the IgA molecules purified from the serum. Not all serum IgA is multimeric (i.e., contains J chains), thus the relative abundance of the J chain is low compared to the abundance of the IgA light chains and heavy chains. Mass spectra were obtained for the different glycoforms of the J chains shown in FIGS. 2B and 2C (FIG. 3A). The different glycoforms of the J chain and relative abundance of each are clearly visible in the deconvoluted mass spectrum (FIG. 3B).

Figure 4:
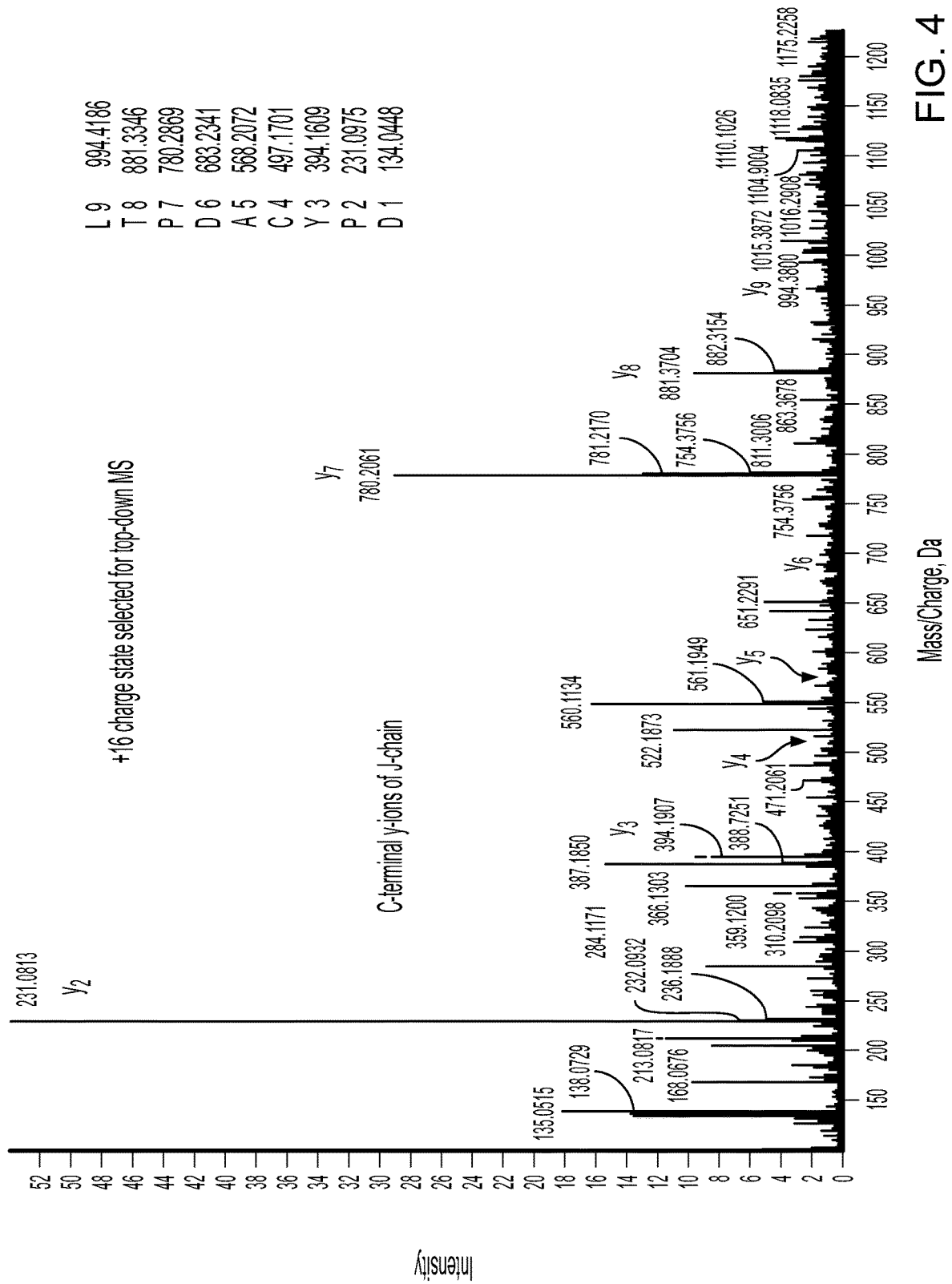
FIG. 4 is a top-down mass spectrum of the +16 charge state from a J chain glycoform fragment (SEQ ID NO:2).

To confirm the identity of the J chain in the sample, a top-down fragment ion mass spectrum was derived from the +16 charge state for a specific J chain glycoform. The spectrum shows the y-ion series from the known amino acids from the C-terminus of the J chain (FIG. 4).

Figure 5:
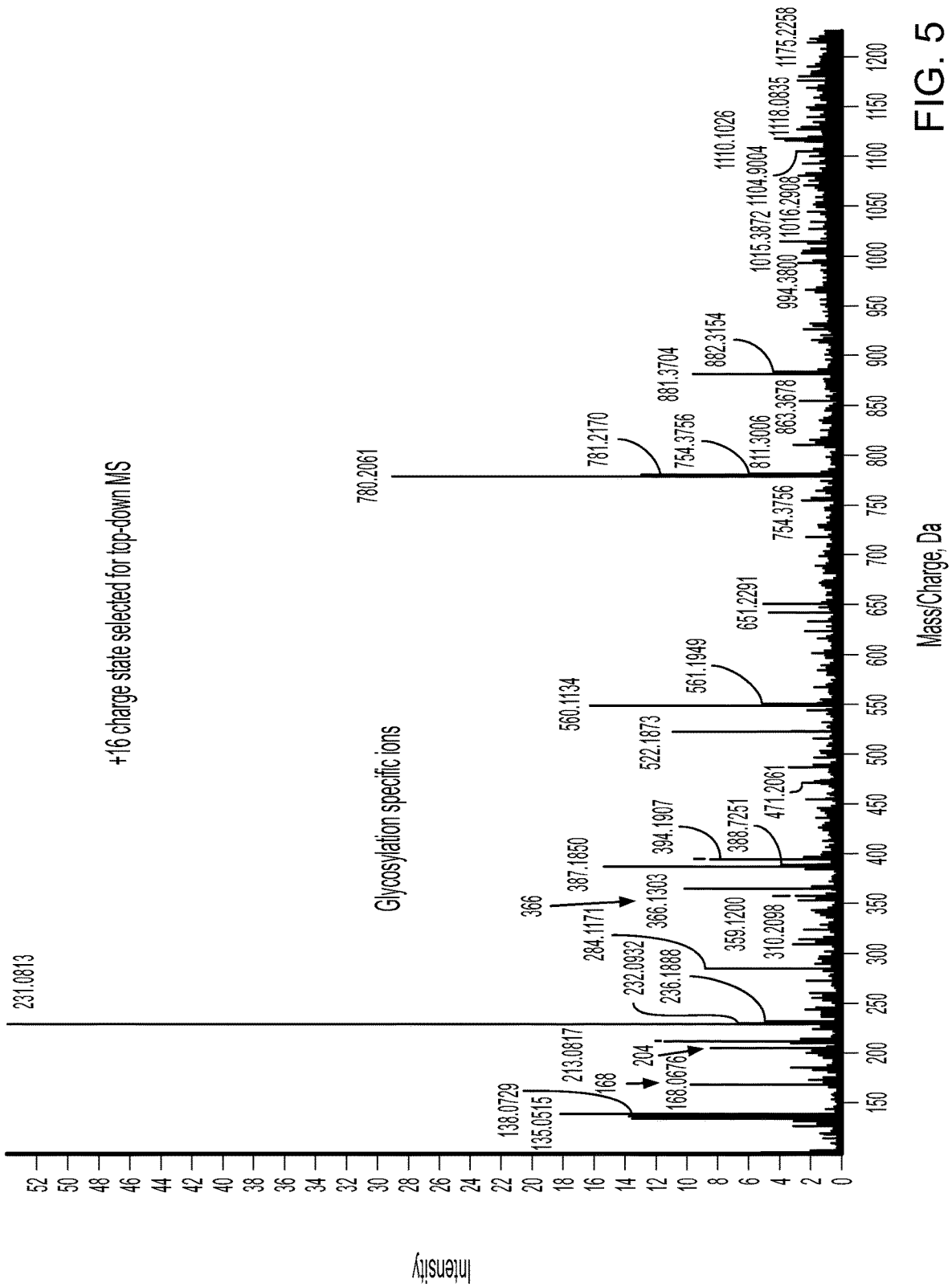
FIG. 5 is a top-down mass spectrum of the +16 charge state from a J chain glycoform fragment with labeled glycosylation specific fragments at m/z 168, 204, and 366.

To examine whether the J chains observed are glycosylated, a top-down fragment ion mass spectrum was derived from the +16 charge state for a specific J chain glycoform. The spectrum shows the glycosylation specific fragment ions that can only come from a glycosylated protein (FIG. 5).

Figure 6A:
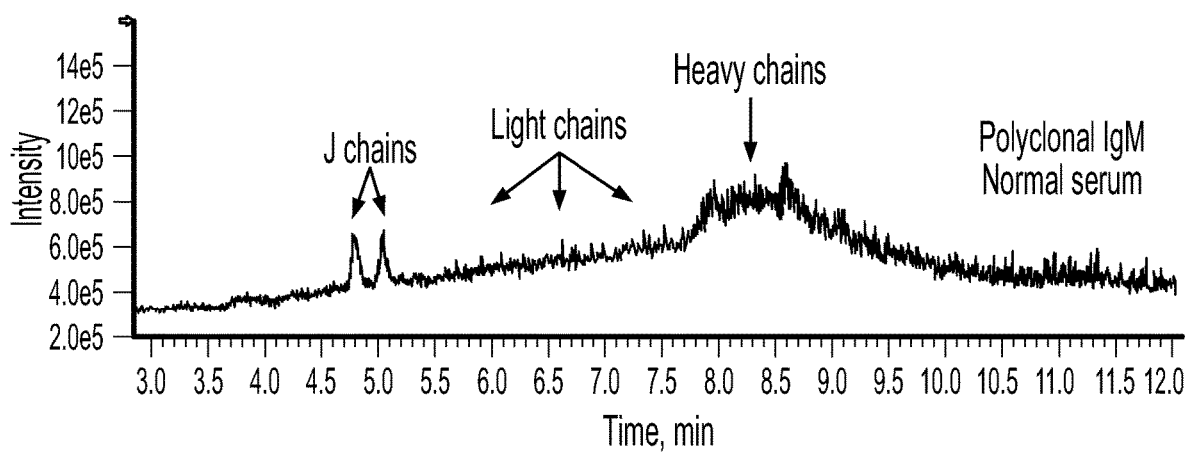
FIGS. 6A-6C contain MS spectra of polyclonal IgM. A) A TIC of polyclonal IgM in a pooled sample of normal human serum. B) An extracted TIC specific for peaks from a glycosylated J chain (glycoform 2). C) An extracted TIC specific for peaks from a glycosylated J chain (glycoform 1).
Figure 6B:
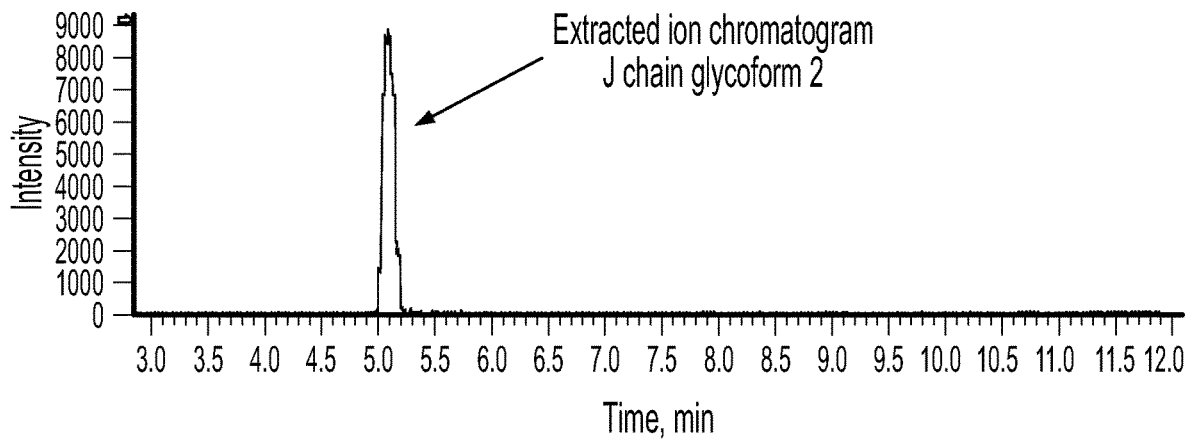
Figure 6C:
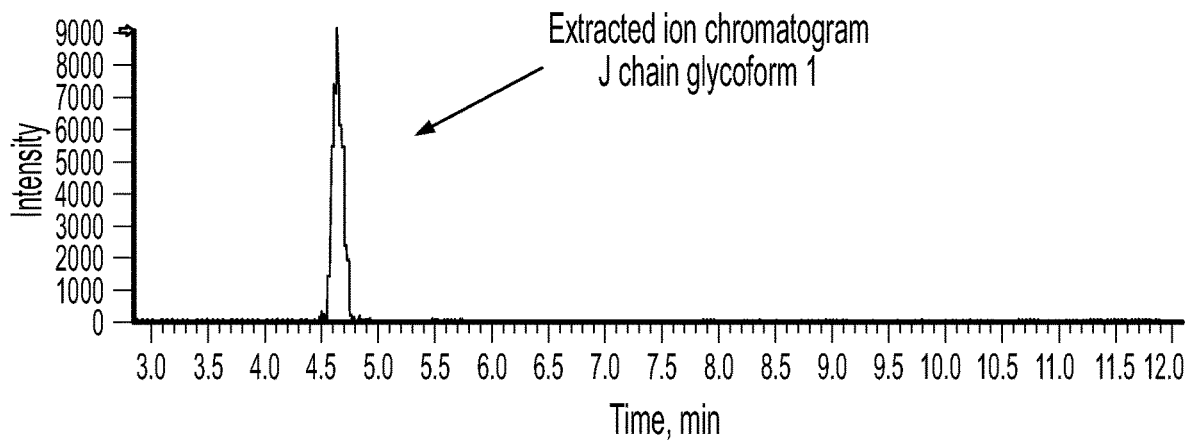
Figure 7A:
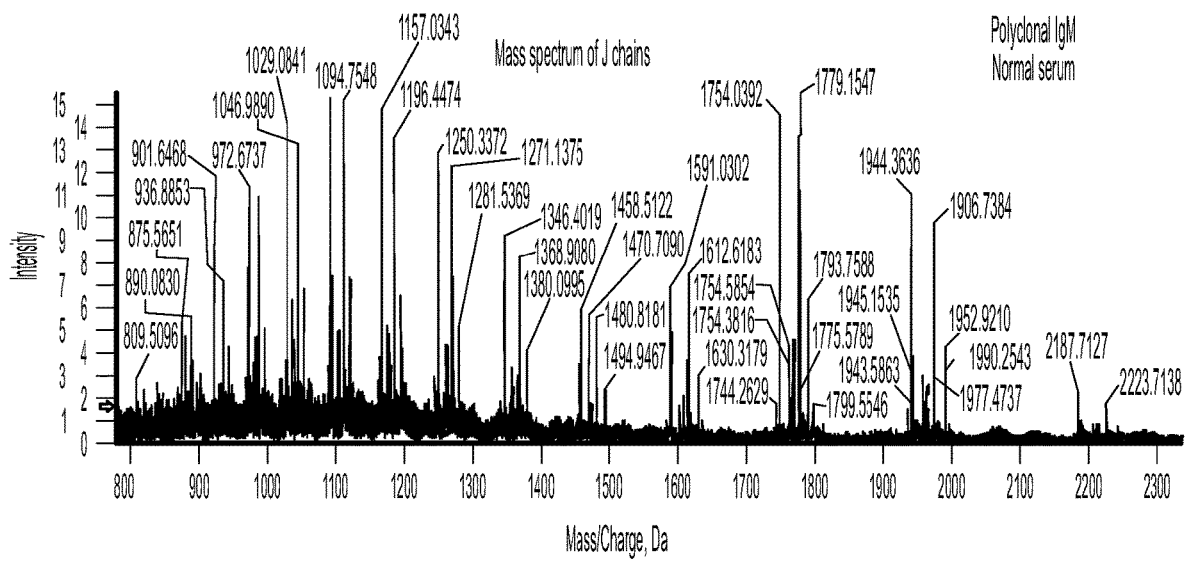
FIGS. 7A-7B contain MS spectra of different glycoforms of IgM J chains. A) A summed mass spectrum of J chains from the peaks in FIGS. 6B and 2C. B) A deconvoluted mass spectrum of J chains from the peaks in FIGS. 6B and 6C.
Figure 7B:
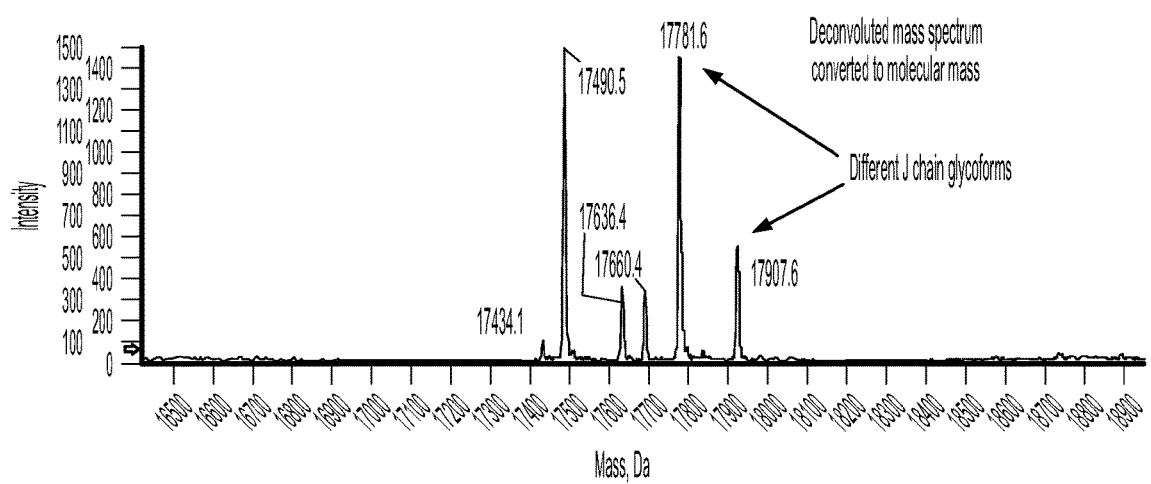

IgM was purified using camelid nanobody beads from normal pooled serum and subjected to MS (FIG. 6A). Extracted ion chromatograms specific for peaks from the J chain (FIGS. 6B and 6C) show the relative abundance of the J chain compared to all the IgM molecules purified from the serum. All serum IgM is multimeric (i.e., contains J chains), thus the relative abundance of the J chain is larger compared to IgA. This also confirmed that the relative abundance of the J chain to IgM is greater as compared to the relative abundance of the J chain to IgA since the same serum was used for each experiment. Mass spectra were obtained for the different glycoforms of the J chains shown in FIGS. 6B and 6C (FIG. 7A). The different glycoforms of the J chain and relative abundance of each are clearly visible in the deconvoluted mass spectrum (FIG. 7B).

Figure 8A:
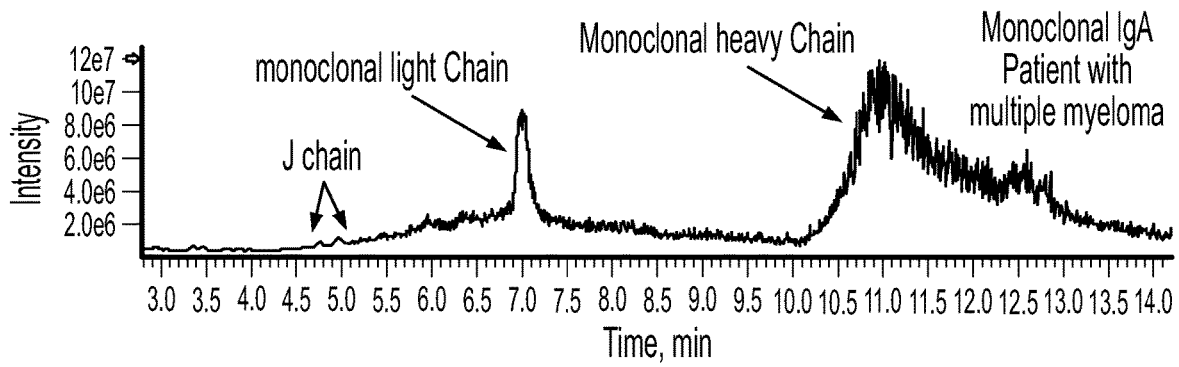
FIGS. 8A-8C contain MS spectra of monoclonal IgA. A) A TIC of monoclonal IgA in a serum sample from a human multiple myeloma patient. B) An extracted TIC specific for peaks from a glycosylated J chain (glycoform 2). C) An extracted TIC specific for peaks from a glycosylated J chain (glycoform 1).
Figure 8B:
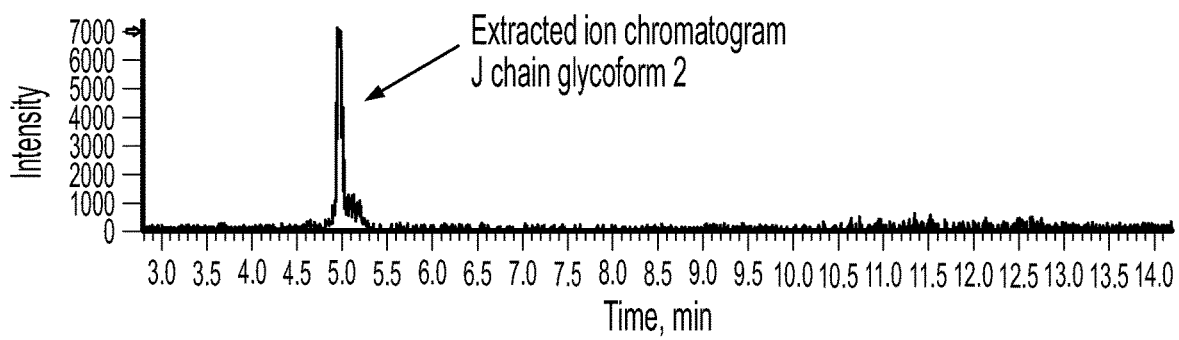
Figure 8C:
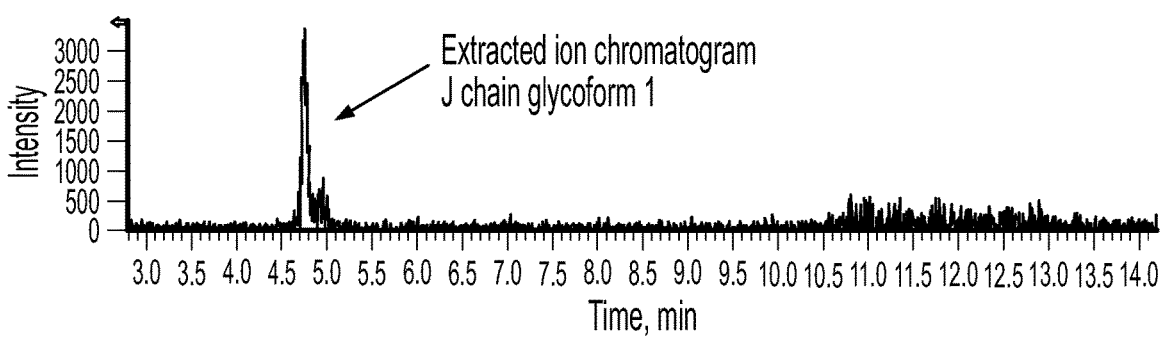

IgA was purified using camelid nanobody beads from serum from a patient with multiple myeloma and subjected to MS (FIG. 8A). Extracted ion chromatograms specific for peaks from the J chain (FIGS. 8B and 8C) show the relative abundance of the J chain compared to the monoclonal IgA light chain and heavy chain purified from serum. Mass spectra were obtained for the different glycoforms of the J chains shown in FIGS. 8B and 8C (FIG. 9A). The different glycoforms of the J chain and relative abundance of each are clearly visible in the deconvoluted mass spectrum (FIG. 9B). The relative abundance of each IgA J chain glycoform in MM was nearly identical to the abundances observed in normal serum (compare FIG. 3B and FIG. 9B).

Figure 10A:
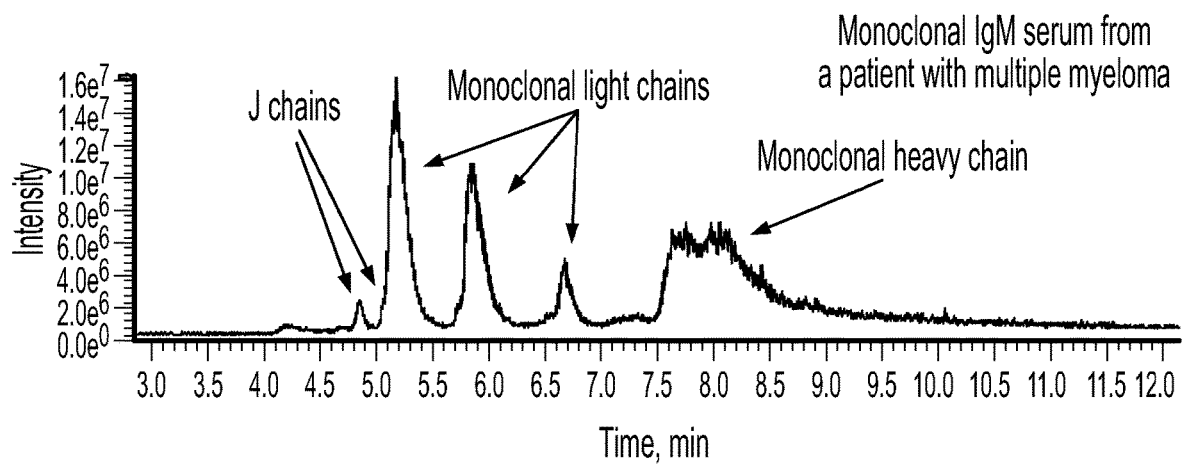
FIGS. 10A-10C contain MS spectra of monoclonal IgM. A) A TIC of monoclonal IgM in a serum sample from a human multiple myeloma patient. B) An extracted TIC specific for peaks from a glycosylated J chain (glycoform 2). C) An extracted TIC specific for peaks from a glycosylated J chain (glycoform 1).
Figure 10B:
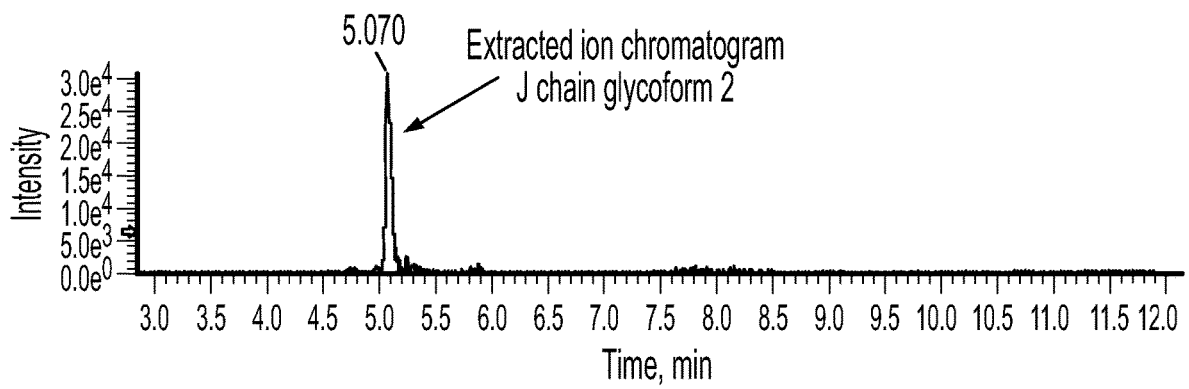
Figure 10C:
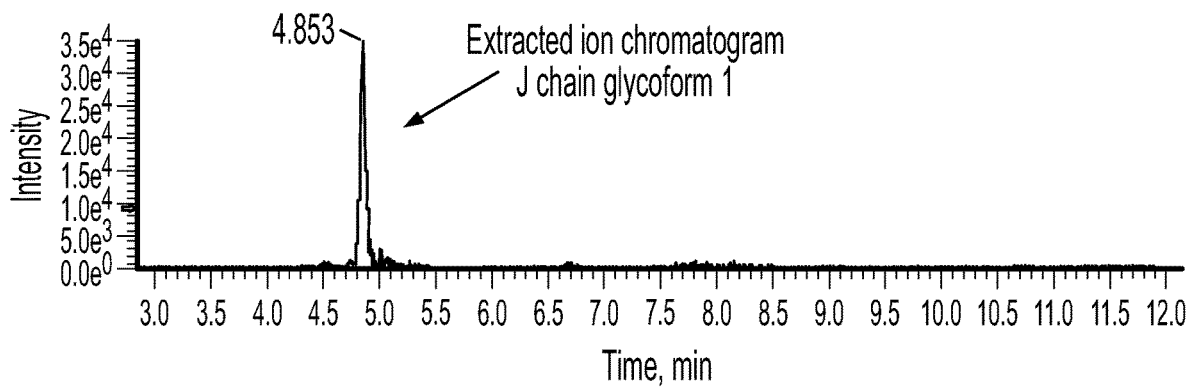

IgM was purified using camelid nanobody beads from serum from a patient with multiple myeloma and subjected to MS (FIG. 10A). Extracted ion chromatograms specific for peaks from the J chain (FIGS. 10B and 10C) show the relative abundance of the J chain compared to the monoclonal IgM light chain and heavy chain purified from serum. Mass spectra were obtained for the different glycoforms of the J chains shown in FIGS. 10B and 10C (FIG. 11A). The different glycoforms of the J chain and relative abundance of each are clearly visible in the deconvoluted mass spectrum (FIG. 11B). The relative abundance of each IgM J chain glycoform in MM was nearly identical to the abundances observed in normal serum (compare FIG. 7B and FIG. 11B).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying J chains in a sample, the method comprising:
   providing a sample comprising immunoglobulins;
   immunopurifying IgA immunoglobulins and/or IgM immunoglobulins from the sample;
   subjecting the immunopurified immunoglobulins to a top-down mass spectrometry technique to obtain a mass spectrum of the sample; and
   identifying the presence of J chains based on the multiply charged ion peaks in the spectrum corresponding to the J chains.

2. The method of claim 1, the method further comprising: converting the peak area of the identified peaks to a molecular mass to quantify the J chains in the sample.

3. The method of claim 1, comprising immunopurifying IgA from the sample, wherein said immunopurifying comprises using an anti-human IgA antibody or immunopurifying IgM from the sample, wherein said immunopurifying comprises using an anti-human IgM antibody.

4. The method of claim 1, wherein said immunopurifying comprises using a non-human antibody, and wherein said non-human antibody is a camelid antibody, a cartilaginous fish antibody, llama, sheep, goat, rabbit, or a mouse antibody.

5. The method of claim 4, wherein said antibody is a single domain antibody fragment.

6. The method of claim 1, wherein said IgA immunoglobulins are multimeric IgA immunoglobulins.

7. The method of claim 1, wherein said method further comprises determining the ratio of J chains to IgA immunoglobulins.

8. The method of claim 1, wherein said IgM immunoglobulins are multimeric IgM immunoglobulins.

9. The method of claim 1, wherein said method further comprises determining the ratio of J chains to IgM immunoglobulins.

10. The method of claim 1, wherein said immunoglobulins are not fragmented during the mass spectrometry technique.

11. The method of claim 1, wherein said sample is selected from the group consisting of blood, serum, plasma, urine, lachrymal fluid, and saliva.

12. The method of claim 1, wherein said mass spectrometry technique comprises a liquid chromatography-mass spectrometry (LC-MS) technique.

13. The method of claim 12, wherein the mass spectrometry technique is electrospray ionization mass spectrometry (ESI-MS).

14. The method of claim 13, wherein the ESI-MS technique comprises a quadrupole time-of-flight (TOF) mass spectrometer.

15. The method of claim 1, wherein the J chains comprise a post-translational modification.

16. The method of claim 15, wherein said post-translational modification is glycosylation.

17. The method of claim 1, wherein the J chains lack a post-translational modification.

18. A method for treating a disorder in a patient, wherein said disorder is associated with abnormal production of IgA immunoglobulins and/or IgM immunoglobulins, the method comprising:
   identifying said patient as having said disorder, said identifying comprising:
      providing a sample comprising immunoglobulins from said patient;
      immunopurifying IgA immunoglobulins and/or IgM immunoglobulins from the sample;
      subjecting the immunopurified immunoglobulins to a top-down mass spectrometry technique to obtain a mass spectrum of the sample;
      identifying the presence of J chains based on the multiply charged ion peaks in the spectrum corresponding to the J chains;
      determining the ratio of J chains to IgA immunoglobulins and/or the ratio of J chains to IgM immunoglobulins in the sample; and
      comparing the ratio to a reference value; and
   administering to said patient a therapeutic agent to treat said disorder.

19. The method of claim 18, further comprising performing a plasma exchange or a stem cell transplant.

20. A method of monitoring a treatment of a disorder in a patient, wherein said disorder is associated with abnormal production of IgA immunoglobulins and/or IgM immunoglobulins, the method comprising:
   providing an initial sample comprising immunoglobulins from the patient, wherein said initial sample is obtained from the patient prior to the treatment;
   providing one or more secondary samples comprising immunoglobulins, wherein said one or more secondary samples are obtained from the patient during the treatment, after the treatment, or both;
   immunopurifying IgA immunoglobulins and/or IgM immunoglobulins from the samples;
   subjecting the immunopurified immunoglobulins to a top-down mass spectrometry technique to obtain a mass spectrum of the samples;
   identifying the presence of J chains in said samples based on the multiply charged ion peaks in the spectrum corresponding to the J chains;
   determining the ratio of J chains to IgA immunoglobulins and/or the ratio of J chains to IgM immunoglobulins in the samples; and
   comparing the ratios from the initial sample and the one or more secondary samples.

21. The method of claim 18, wherein said disorder is selected from the group consisting of multiple myeloma, asymptomatic or smoldering multiple myeloma, solitary plasmacytoma, monoclonal gammopathy of undetermined significance, B-cell chronic lymphocytic leukemia, Waldenstrom macrogloblinemia, non-secretory myeloma, selective IgA deficiency, selective IgM deficiency, celiac disease, IgA nephropathy, autoimmune disorders, and neurologic diseases.

22. The method of claim 18, wherein said patient is a human.

23. The method of claim 18, wherein said immunopurifying comprises using a non-human antibody, and wherein said non-human antibody is a camelid antibody, a cartilaginous fish antibody, llama, sheep, goat, rabbit, or a mouse antibody.

24. The method of claim 23, wherein said non-human antibody is a single domain antibody fragment.

25. The method of claim 18, wherein said immunoglobulins are not fragmented during the mass spectrometry technique.

26. The method of claim 18, wherein said sample is selected from the group consisting of blood, serum, plasma, urine, lachrymal fluid, and saliva.

27. The method of claim 18, wherein said mass spectrometry technique comprises a liquid chromatography-mass spectrometry (LC-MS) technique.

28. The method of claim 18, wherein the mass spectrometry technique is electrospray ionization mass spectrometry (ESI-MS).

29. The method of claim 28, wherein the ESI-MS technique comprises a quadrupole time-of-flight (TOF) mass spectrometer.

* * * * *

UNITED STATES PATENT AND TRADEMARK OFFICE
CERTIFICATE OF CORRECTION

PATENT NO. : 12,153,052 B2
APPLICATION NO. : 16/646279
DATED : November 26, 2024
INVENTOR(S) : Murray et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1163 days.

Signed and Sealed this
Twelfth Day of August, 2025

Coke Morgan Stewart
*Acting Director of the United States Patent and Trademark Office*